(12) United States Patent
Wardle

(10) Patent No.: US 9,510,973 B2
(45) Date of Patent: Dec. 6, 2016

(54) OCULAR IMPLANTS DEPLOYED IN SCHLEMM'S CANAL OF THE EYE

(75) Inventor: John Wardle, San Clemente, CA (US)

(73) Assignee: IVANTIS, INC., Irvine, CA (US)

(*) Notice: Subject to any disclaimer, the term of this patent is extended or adjusted under 35 U.S.C. 154(b) by 838 days.

(21) Appl. No.: 13/167,644

(22) Filed: Jun. 23, 2011

(65) Prior Publication Data

US 2011/0319806 A1 Dec. 29, 2011

Related U.S. Application Data

(60) Provisional application No. 61/357,900, filed on Jun. 23, 2010.

(51) Int. Cl.
| A61M 27/00 | (2006.01) |
| A61F 9/00 | (2006.01) |
| A61F 9/007 | (2006.01) |

(52) U.S. Cl.
CPC .................. *A61F 9/00781* (2013.01)

(58) Field of Classification Search
CPC .................................... A61F 9/000781
USPC .................................. 604/8, 9, 10
See application file for complete search history.

(56) References Cited

U.S. PATENT DOCUMENTS

| 703,296 A | 6/1902 | Arnold |
| 1,601,709 A | 10/1926 | Windom |
| 2,716,983 A | 9/1955 | George et al. |
| 3,071,135 A | 1/1963 | Baldwin et al. |
| 3,788,327 A | 1/1974 | Donowitz et al. |
| 3,811,442 A | 5/1974 | Maroth |
| 3,948,271 A | 4/1976 | Akiyama |
| 4,037,604 A | 7/1977 | Newkirk |
| 4,428,746 A | 1/1984 | Mendez |
| 4,457,757 A | 7/1984 | Molteno |
| 4,601,713 A | 7/1986 | Fuquo |
| 4,689,040 A | 8/1987 | Thompson |
| 4,699,140 A | 10/1987 | Holmes et al. |
| 4,706,669 A | 11/1987 | Schlegel |
| 4,722,724 A | 2/1988 | Schocket |
| 4,733,665 A | 3/1988 | Palmaz |

(Continued)

FOREIGN PATENT DOCUMENTS

| AU | 1998/76197 B2 | 2/1999 |
| CN | 1950091 A | 4/2007 |

(Continued)

OTHER PUBLICATIONS

Wardle et al.,; U.S. Appl. No. 13/160,355 entitled "Ocular implants for delivery into the eye," filed Jun. 14, 2011.

(Continued)

*Primary Examiner* — Philip R Wiest
*Assistant Examiner* — Benjamin Klein
(74) *Attorney, Agent, or Firm* — Shay Glenn LLP

(57) ABSTRACT

An ocular implant is provided that is adapted to reside at least partially in a portion of Schlemm's canal of an eye. The implant includes an implant body having plurality of filars extending along a longitudinal axis of the implant. The implant is configured to move between a radially collapsed state and a radially expanded state. In some embodiments, the implant is configured to assume the radially expanded state when no external forces are acting thereon. Methods of delivering and using the ocular implant are also provided.

12 Claims, 25 Drawing Sheets

(56) References Cited

U.S. PATENT DOCUMENTS

| | | |
|---|---|---|
| 4,750,901 A | 6/1988 | Molteno |
| 4,826,478 A | 5/1989 | Schocket |
| 4,861,341 A | 8/1989 | Woodburn |
| 4,880,000 A | 11/1989 | Holmes et al. |
| 4,886,488 A | 12/1989 | White |
| 4,919,130 A | 4/1990 | Stoy et al. |
| 4,934,363 A | 6/1990 | Smith et al. |
| 4,936,825 A | 6/1990 | Ungerleider |
| 4,946,436 A | 8/1990 | Smith |
| 4,968,296 A | 11/1990 | Ritch et al. |
| 5,092,837 A | 3/1992 | Ritch et al. |
| 5,127,901 A | 7/1992 | Odrich |
| 5,178,604 A | 1/1993 | Baerveldt et al. |
| 5,180,362 A | 1/1993 | Worst |
| 5,190,552 A | 3/1993 | Kelman |
| 5,213,569 A | 5/1993 | Davis |
| 5,246,452 A | 9/1993 | Sinnott |
| 5,290,267 A | 3/1994 | Zimmermann |
| 5,360,399 A | 11/1994 | Stegmann |
| 5,372,577 A | 12/1994 | Ungerleider |
| 5,445,637 A | 8/1995 | Bretton |
| 5,454,796 A | 10/1995 | Krupin |
| 5,458,615 A | 10/1995 | Klemm et al. |
| 5,536,259 A | 7/1996 | Utterberg |
| 5,575,780 A | 11/1996 | Saito |
| 5,591,223 A | 1/1997 | Lock et al. |
| 5,613,972 A | 3/1997 | Lee et al. |
| 5,626,558 A | 5/1997 | Suson |
| 5,653,753 A | 8/1997 | Brady et al. |
| 5,676,669 A | 10/1997 | Colvard |
| 5,792,099 A | 8/1998 | DeCamp et al. |
| 5,807,302 A | 9/1998 | Wandel |
| 5,865,831 A | 2/1999 | Cozean et al. |
| 5,868,697 A | 2/1999 | Richter et al. |
| 5,879,319 A | 3/1999 | Pynson et al. |
| 5,893,837 A | 4/1999 | Eagles et al. |
| 5,919,171 A | 7/1999 | Kira et al. |
| 5,948,427 A | 9/1999 | Yamamoto et al. |
| 5,968,058 A | 10/1999 | Richter et al. |
| 6,007,511 A | 12/1999 | Prywes |
| 6,050,970 A | 4/2000 | Baerveldt |
| 6,102,045 A | 8/2000 | Nordquist et al. |
| 6,186,974 B1 | 2/2001 | Allan et al. |
| 6,217,584 B1 | 4/2001 | Nun |
| 6,221,078 B1 | 4/2001 | Bylsma |
| 6,238,409 B1 | 5/2001 | Hojeibane |
| D444,874 S | 7/2001 | Haffner et al. |
| 6,328,747 B1 | 12/2001 | Nun |
| 6,375,642 B1 | 4/2002 | Grieshaber et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,517,523 B1 | 2/2003 | Kaneko et al. |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,551,289 B1 | 4/2003 | Higuchi et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,899,717 B2 | 5/2005 | Weber et al. |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,094,225 B2 | 8/2006 | Tu et al. |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,034,105 B2 | 10/2011 | Stegmann et al. |
| 8,123,729 B2 | 2/2012 | Yamamoto et al. |
| 8,172,899 B2 | 5/2012 | Silvestrini et al. |
| 8,308,701 B2 | 11/2012 | Horvath et al. |
| 8,636,647 B2 | 1/2014 | Silvestrini et al. |
| 8,663,303 B2 | 3/2014 | Horvath et al. |
| 8,939,948 B2 | 1/2015 | De Juan, Jr. et al. |
| 8,945,038 B2 | 2/2015 | Yablonski |
| 8,951,221 B2 | 2/2015 | Stegmann et al. |
| 8,974,511 B2 | 3/2015 | Horvath et al. |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0052653 A1 | 5/2002 | Durgin |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2002/0165504 A1 | 11/2002 | Sharp et al. |
| 2002/0193805 A1 | 12/2002 | Ott et al. |
| 2003/0004457 A1 | 1/2003 | Andersson |
| 2003/0040754 A1 | 2/2003 | Mitchell et al. |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0060784 A1 | 3/2003 | Hilgers et al. |
| 2003/0093084 A1 | 5/2003 | Nissan et al. |
| 2003/0097151 A1 | 5/2003 | Smedley et al. |
| 2003/0181848 A1 | 9/2003 | Bergheim et al. |
| 2003/0187384 A1 | 10/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0030302 A1 | 2/2004 | Kamata et al. |
| 2004/0082939 A1 | 4/2004 | Berlin |
| 2004/0088048 A1 | 5/2004 | Richter et al. |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0122380 A1 | 6/2004 | Utterberg |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0199171 A1 | 10/2004 | Akahoshi |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |

(56) References Cited

U.S. PATENT DOCUMENTS

| | | |
|---|---|---|
| 2004/0254520 A1 | 12/2004 | Porteous et al. |
| 2004/0260228 A1 | 12/2004 | Lynch et al. |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0244464 A1 | 11/2005 | Hughes |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0288619 A1 | 12/2005 | Gharib et al. |
| 2006/0020247 A1 | 1/2006 | Kagan et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155300 A1 | 7/2006 | Stamper et al. |
| 2006/0167421 A1 | 7/2006 | Quinn |
| 2006/0167466 A1 | 7/2006 | Dusek |
| 2006/0173397 A1 | 8/2006 | Tu et al. |
| 2006/0178674 A1 | 8/2006 | McIntyre |
| 2006/0189915 A1 | 8/2006 | Camras et al. |
| 2006/0189916 A1 | 8/2006 | Bas |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0241749 A1 | 10/2006 | Tu et al. |
| 2006/0264971 A1 | 11/2006 | Akahoshi |
| 2006/0276759 A1 | 12/2006 | Kinast et al. |
| 2007/0010827 A1 | 1/2007 | Tu et al. |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0135681 A1 | 6/2007 | Chin et al. |
| 2007/0179520 A1 | 8/2007 | West |
| 2007/0191863 A1 | 8/2007 | De Juan, Jr. et al. |
| 2007/0202186 A1 | 8/2007 | Yamamoto et al. |
| 2007/0219509 A1 | 9/2007 | Tashiro et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0228127 A1 | 9/2008 | Burns et al. |
| 2008/0288082 A1 | 11/2008 | Deal |
| 2008/0312661 A1 | 12/2008 | Downer et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0036843 A1 | 2/2009 | Erskine |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082860 A1 | 3/2009 | Schieber et al. |
| 2009/0082862 A1 | 3/2009 | Schieber et al. |
| 2009/0104248 A1 | 4/2009 | Rapacki et al. |
| 2009/0132040 A1 | 5/2009 | Frion et al. |
| 2009/0138081 A1 | 5/2009 | Bergheim et al. |
| 2009/0182421 A1 | 7/2009 | Silvestrini et al. |
| 2009/0198248 A1 | 8/2009 | Yeung et al. |
| 2009/0204053 A1 | 8/2009 | Nissan et al. |
| 2009/0227934 A1 | 9/2009 | Euteneuer et al. |
| 2009/0247955 A1 | 10/2009 | Yamamoto et al. |
| 2009/0259126 A1 | 10/2009 | Saal et al. |
| 2009/0281520 A1 | 11/2009 | Highley et al. |
| 2010/0004580 A1 | 1/2010 | Lynch et al. |
| 2010/0057072 A1 | 3/2010 | Roman et al. |
| 2010/0114309 A1 | 5/2010 | de Juan et al. |
| 2010/0121342 A1 | 5/2010 | Schieber et al. |
| 2010/0137981 A1* | 6/2010 | Silvestrini et al. ............... 604/8 |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0222733 A1 | 9/2010 | Schieber et al. |
| 2010/0234726 A1 | 9/2010 | Sirimanne et al. |
| 2010/0234790 A1 | 9/2010 | Tu et al. |
| 2011/0009874 A1 | 1/2011 | Wardle et al. |
| 2011/0009958 A1 | 1/2011 | Wardle et al. |
| 2011/0098809 A1 | 4/2011 | Wardle et al. |
| 2011/0196487 A1 | 8/2011 | Badawi et al. |
| 2011/0224597 A1 | 9/2011 | Stegmann et al. |
| 2012/0010702 A1 | 1/2012 | Stegmann et al. |
| 2012/0022424 A1 | 1/2012 | Yamamoto et al. |
| 2012/0035524 A1* | 2/2012 | Silvestrini ........................ 604/8 |
| 2012/0136439 A1 | 5/2012 | Schieber et al. |
| 2012/0191064 A1 | 7/2012 | Conston et al. |
| 2012/0271272 A1 | 10/2012 | Hammack et al. |
| 2013/0006165 A1 | 1/2013 | Euteneuer et al. |
| 2013/0079701 A1 | 3/2013 | Schieber et al. |
| 2013/0150959 A1 | 6/2013 | Schieber et al. |
| 2014/0018720 A1 | 1/2014 | Horvath et al. |
| 2014/0066821 A1 | 3/2014 | Freidland et al. |
| 2014/0066831 A1 | 3/2014 | Silvestrini et al. |
| 2015/0057591 A1 | 2/2015 | Horvath et al. |

FOREIGN PATENT DOCUMENTS

| | | |
|---|---|---|
| DE | 4226476 C1 | 8/1993 |
| DE | 19840047 A1 | 3/2000 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| JP | H10-504978 A | 5/1998 |
| JP | 11123205 | 5/1999 |
| JP | 2002542872 | 12/2002 |
| JP | 2006517848 | 8/2006 |
| JP | 2006289075 A | 10/2006 |
| JP | 2010509003 | 3/2010 |
| JP | 2011502649 | 1/2011 |
| WO | WO 00/07525 A1 | 2/2000 |
| WO | WO 00/64389 A1 | 11/2000 |
| WO | WO 00/64393 A1 | 11/2000 |
| WO | WO 01/97727 A1 | 12/2001 |

(56) References Cited

FOREIGN PATENT DOCUMENTS

| WO | WO 02/36052 A1 | 5/2002 |
|----|----|----|
| WO | WO 02/074052 A2 | 9/2002 |
| WO | WO 02/080811 A2 | 10/2002 |
| WO | WO 03/015659 A2 | 2/2003 |
| WO | WO 03/045290 A1 | 6/2003 |
| WO | WO 2004/054643 A1 | 7/2004 |
| WO | WO 2004/093761 A1 | 11/2004 |
| WO | WO 2005/105197 A2 | 11/2005 |
| WO | WO 2006/066103 A2 | 6/2006 |
| WO | WO 2007/035356 A2 | 3/2007 |
| WO | WO 2007/047744 A2 | 4/2007 |
| WO | WO 2007/087061 A2 | 8/2007 |
| WO | WO2008/002377 A1 | 1/2008 |
| WO | WO 2008/005873 A2 | 1/2008 |
| WO | WO 2009/120960 A2 | 10/2009 |
| WO | WO 2011/053512 A1 | 5/2011 |
| WO | WO 2011/057283 A1 | 5/2011 |
| WO | WO 2011/106781 A1 | 9/2011 |
| WO | WO 2011/150045 A1 | 12/2011 |
| WO | WO 2012/051575 A2 | 4/2012 |

OTHER PUBLICATIONS

Bahler, et al.; Trabecular bypass stents decrease intraocular pressure in cultured human anterior segments; Amer. Journal of Ophthalmology; vol. 138, No. 6; pp. 988-994.e2; Dec. 2004.

D'Ermo, et al.; Our results with the operation of ab externo trabeculotomy; Ophthalmologica; vol. 163; pp. 347-355; 1971.

Ellingsen et al.; Trabeculotomy and sinusotomy in enucleated human eyes; Investigative Ophthalmology; vol. 11; pp. 21-28; Jan. 1972.

Grant; Experimental aqueous perfusion in enucleated human eyes; Archives of Ophthalmology; vol. 69; pp. 783-801; Jun. 1963.

Johnstone et al.; "Microsurgery of Schlemm's Canal and the Human Aqueous Outflow System;" American Journal of Ophthalmology, vol. 76 (6): 906-917; Dec. 1973.

Lee et al.; Aqueous-venous shunt and intraocular pressure. Preliminary report of animal studies; Investigative Ophthalmology; vol. 5; No. 1; pp. 59-64; Feb. 1966.

Moses, Robert; The effect of intraocular pressure on resistance to outflow; Survey of Ophthalmology; vol. 22; No. 2; pp. 88-100; Sep.-Oct. 1977.

Mäepea et al.; The pressures in the episcleral veins, schlemm's canal and the trabecular meshwork in monkeys: effects of changes in intraocular pressure; Exp. Eye Res.; vol. 49; pp. 645-663; 1989.

Rosenquist et al.; Outflow resistanc of enucleated human eyes at two different perfusion pressures and differenct extents of trabeculotomy; Current Eye Res.; vol. 8; No. 12; pp. 1233-1240; 1989.

Savage, James; Gonioscopy in the management of glaucoma; Am. Academy of Ophthalmology; Focal Points; vol. XXIV; No. 3; pp. 1-14; Mar. 2006.

Schultz, Jared; Canaloplasty procedure shows promise for open-angle glaucoma in European study; Ocular Surgery News; vol. 34; Mar. 1, 2007.

Smit et al.; Effects of viscoelastic injection into schlemm's canal in primate and human eyes; J. Am. Academy of Ophthalmology; vol. 109; No. 4; pp. 786-792; Apr. 20002.

Spiegel et al.; Schlemm's canal implant: a new method to lower intraocular pressure in patients with POAG?; Ophthalmic Surgery and Lasers; vol. 30; No. 6; pp. 492-494; Jun. 1999.

Lynch, Mary G.; U.S. Appl. No. 60/131,030 entitled "Devices and methods for treating glaucoma by enhancing aqueous outflow through schlemm's canal and anterior chamber angle ," filed Apr. 26, 1999.

Wardle et al.; U.S. Appl. No. 13/330,592 entitled "Delivering Ocular Implants Into the Eye," filed Dec. 19, 2011.

Schieber et al.; U.S. Appl. No. 13/425,874 entitled "Glaucoma Treatment Method," filed Mar. 21, 2012.

Schieber et al.; U.S. Appl. No. 13/776,592 entitled "Glaucoma Treatment Method," filed Feb. 25, 2013.

Wardle et al.; U.S. Appl. No. 13/744,351 entitled "Suspended goniolens system," filed Jan. 17, 2013.

Wardle et al.; U.S. Appl. No. 13/793,638 entitled "Ocular Implants for Delivery into an Anterior Chamber of the Eye," filed Mar. 11, 2013.

Wardle et al.; U.S. Appl. No. 13/865,770 entitled "Ocular Implants and Methods for Delivering Ocular Implants Into the Eye," filed Apr. 18, 2013.

\* cited by examiner

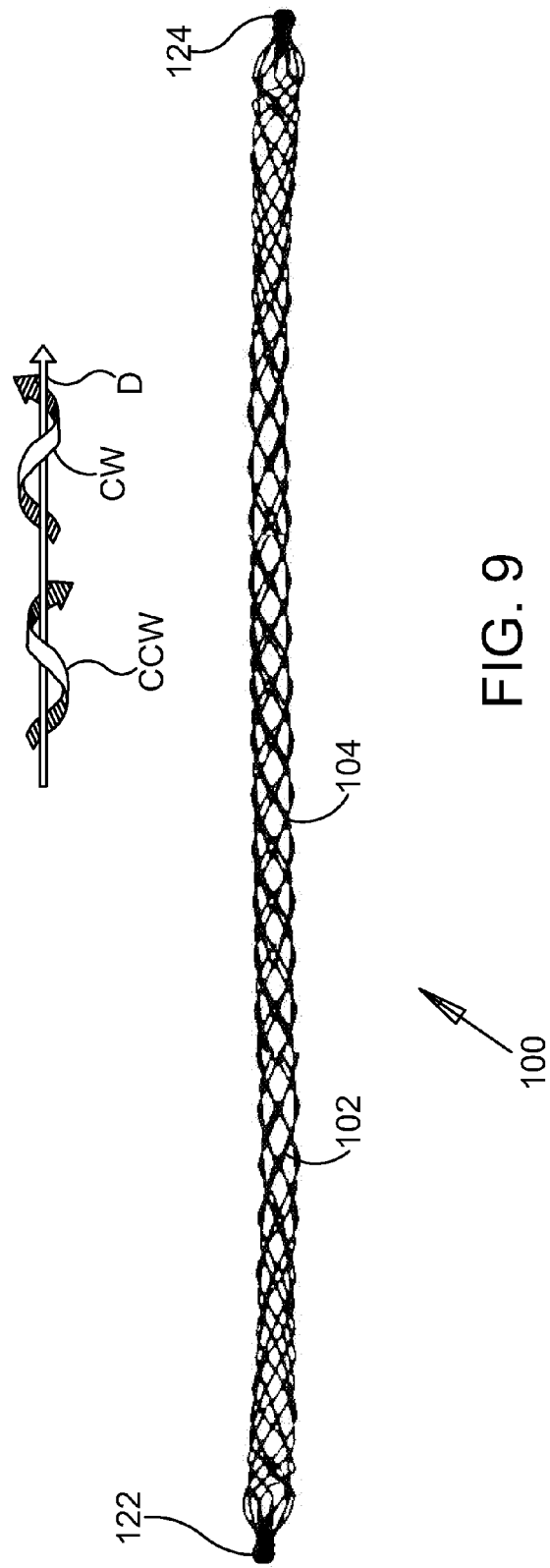

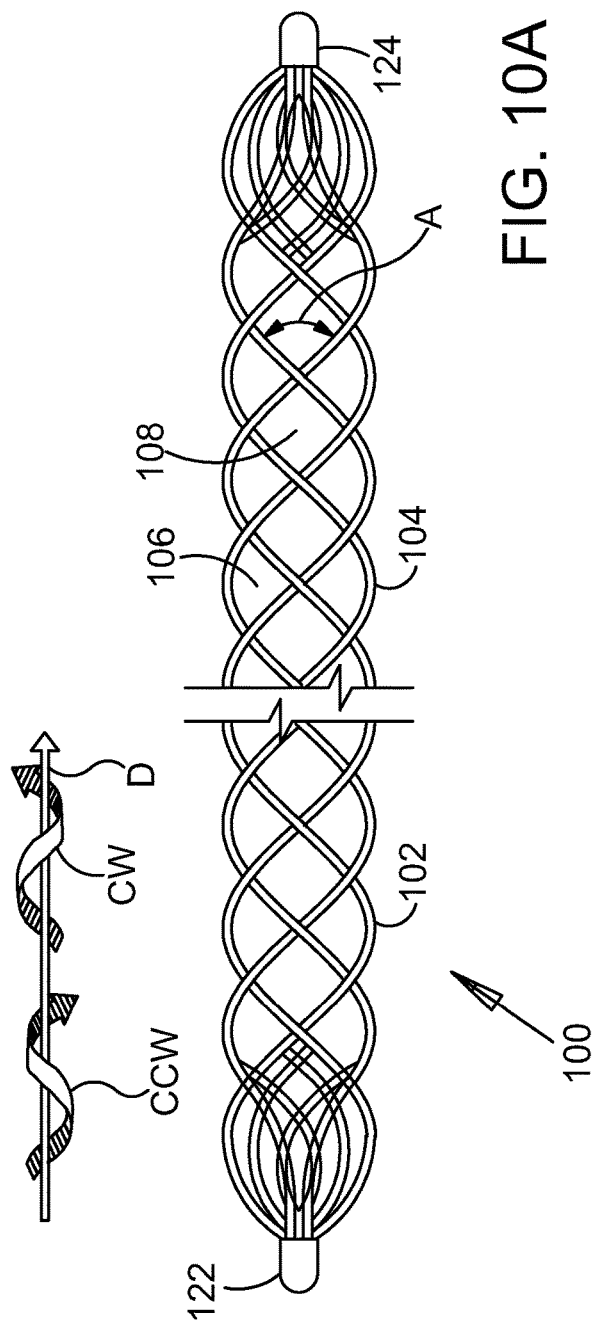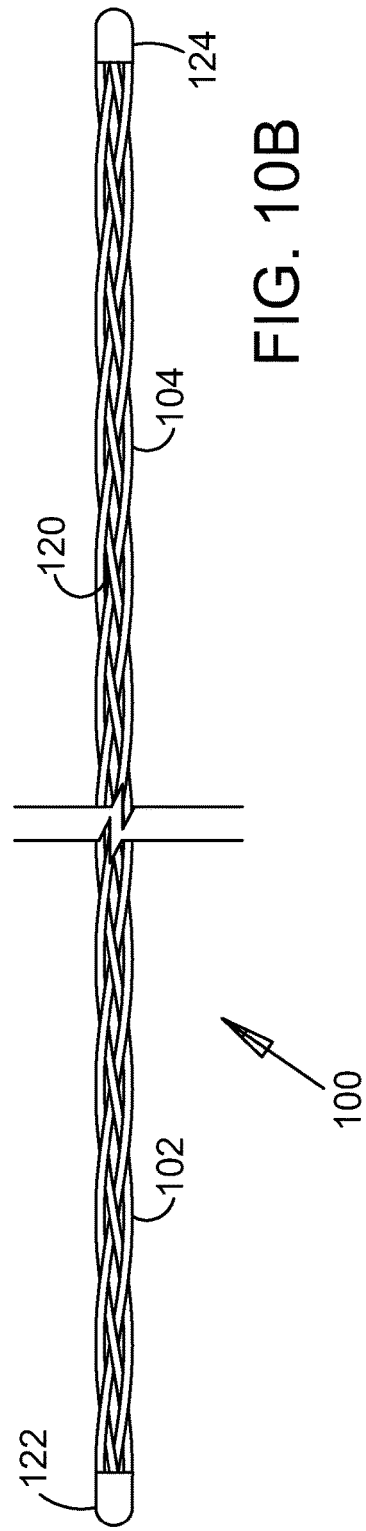

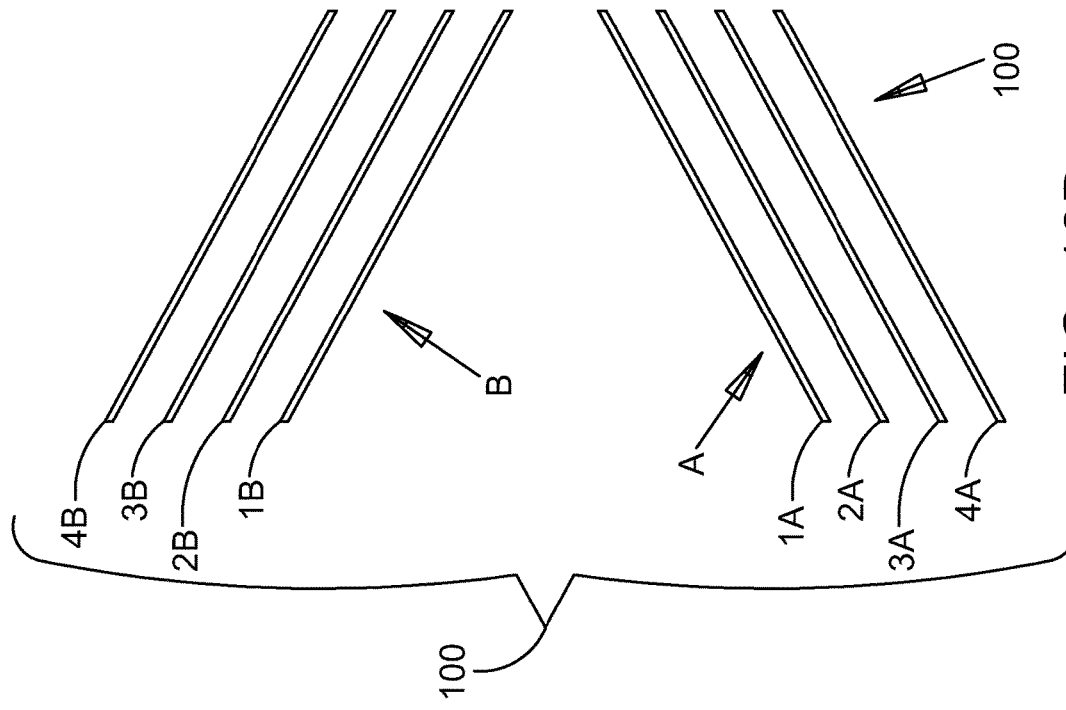
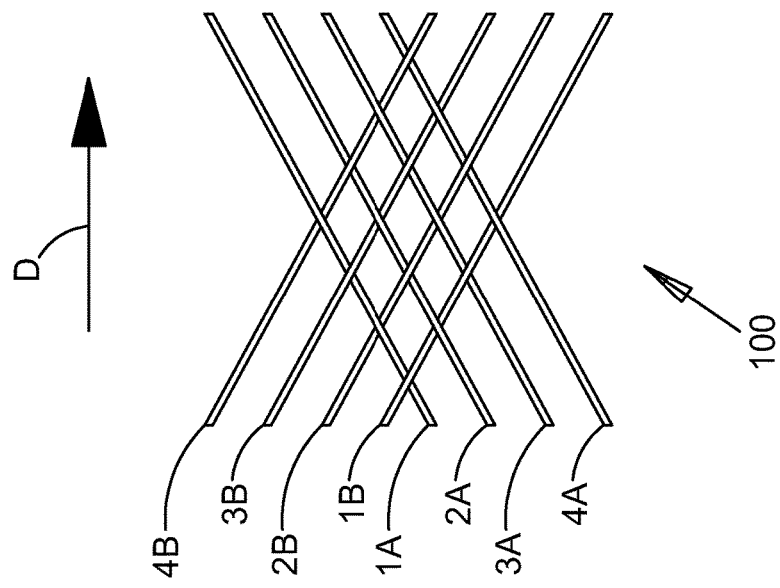

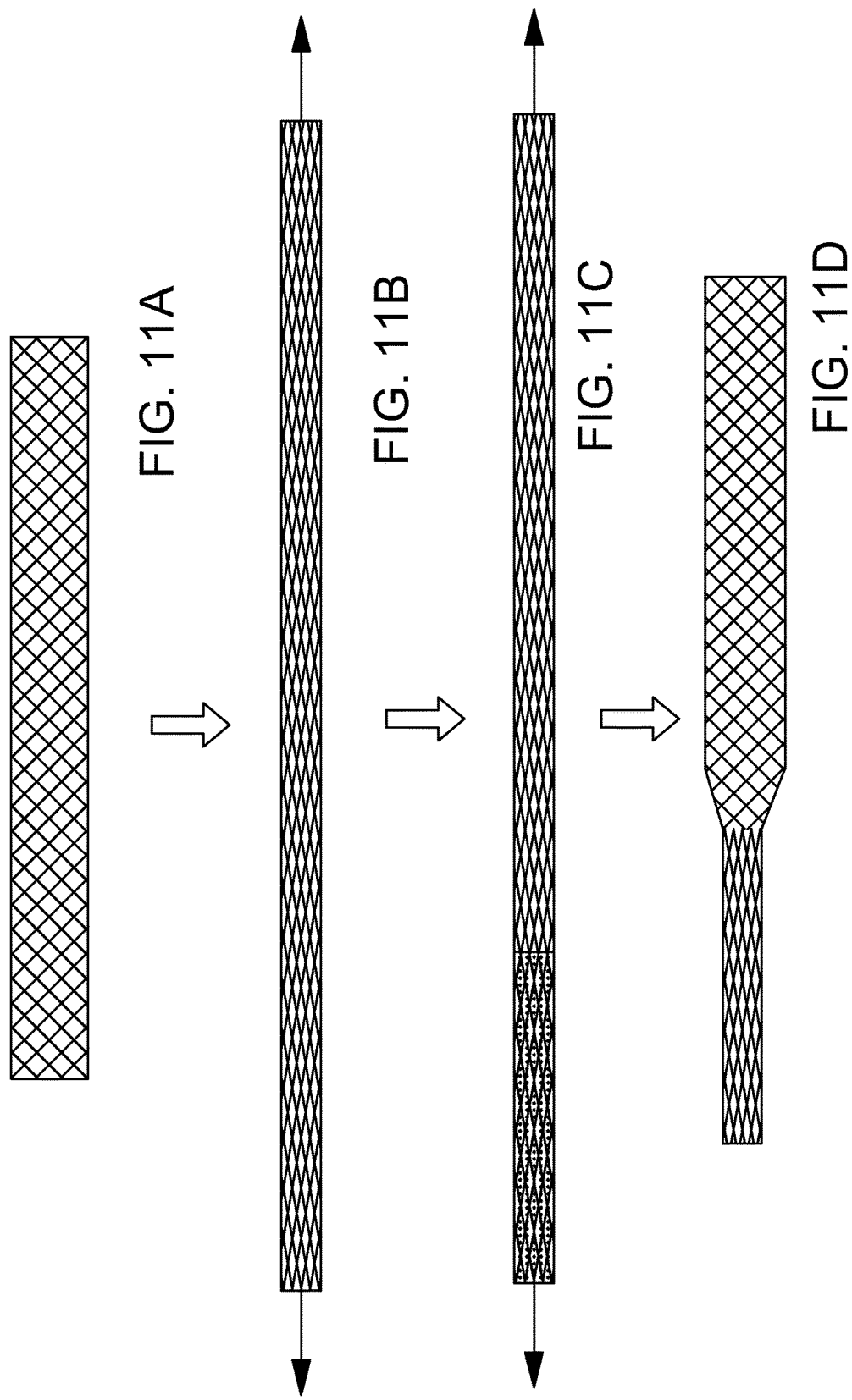

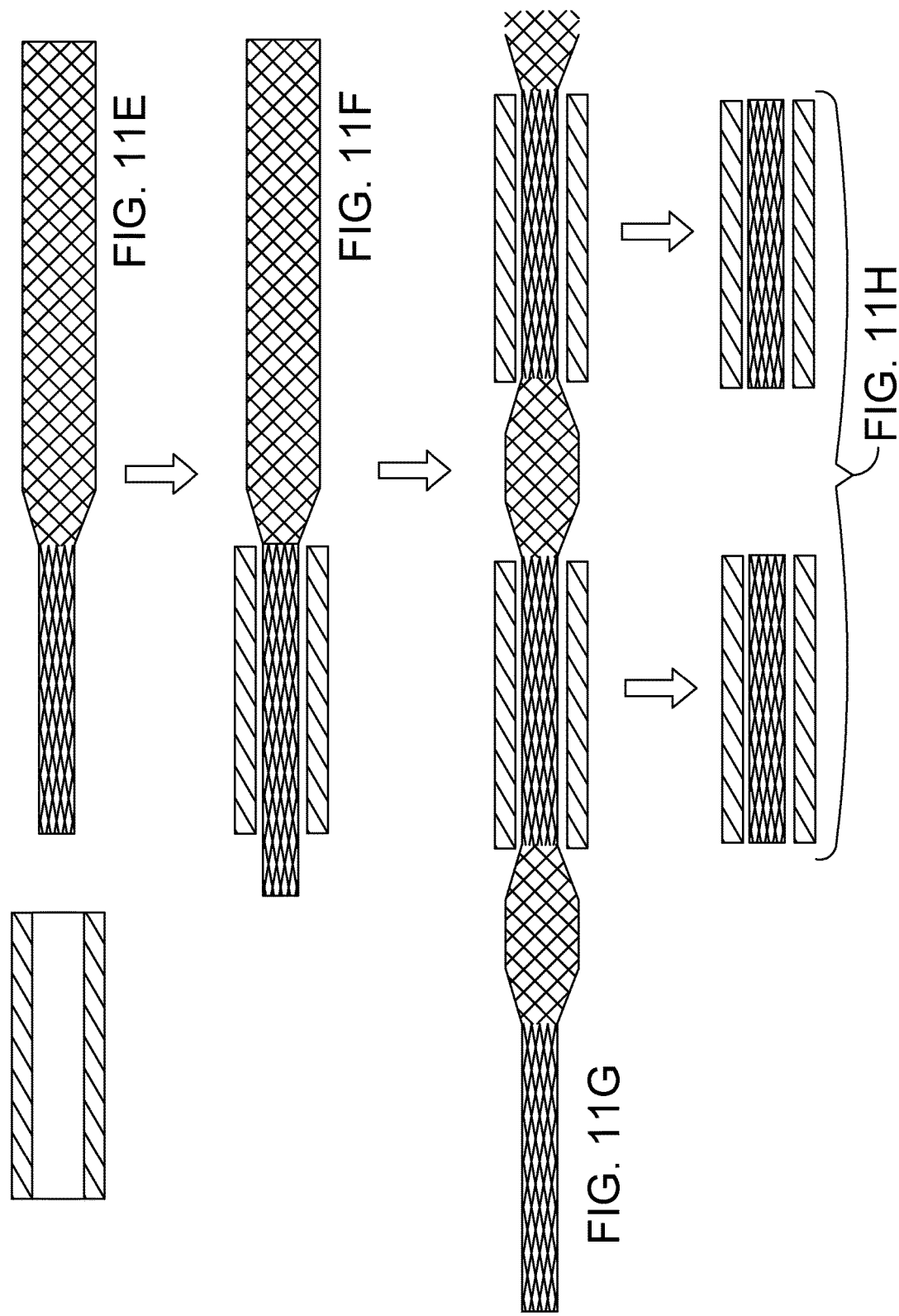

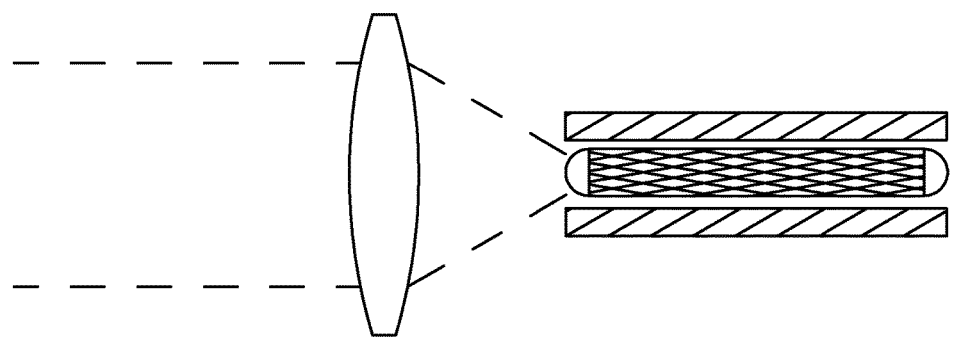
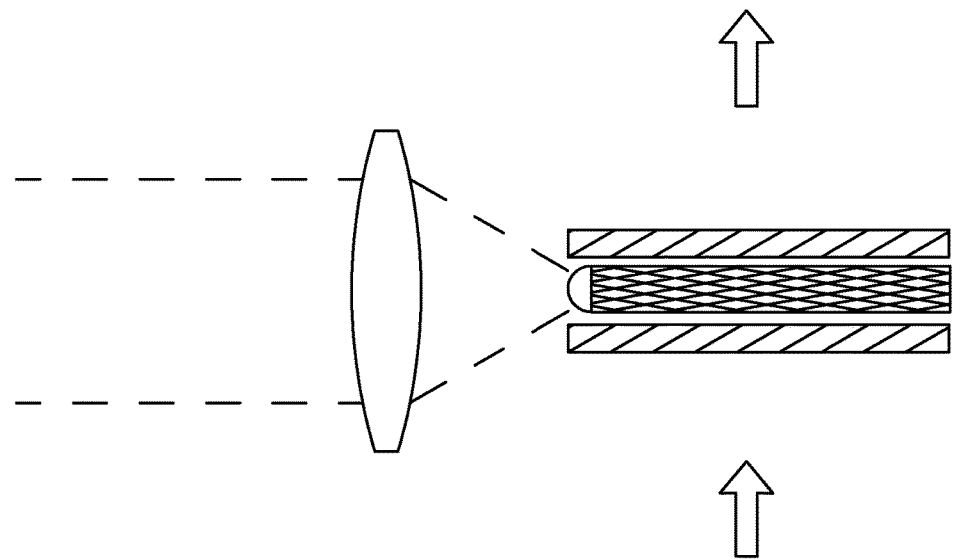
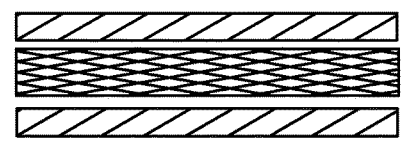

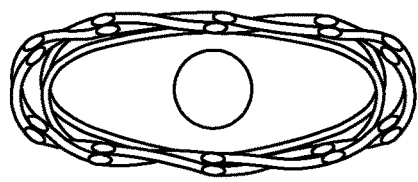
FIG. 13C
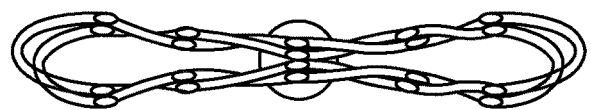
FIG. 13B
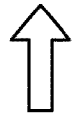
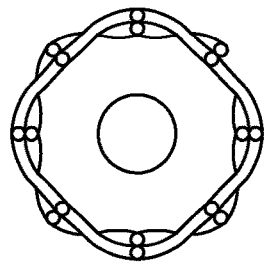
FIG. 13A

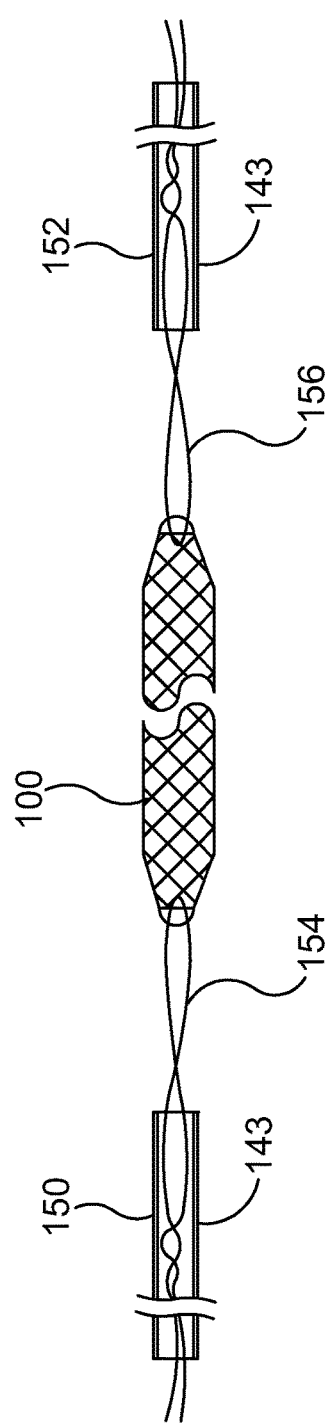
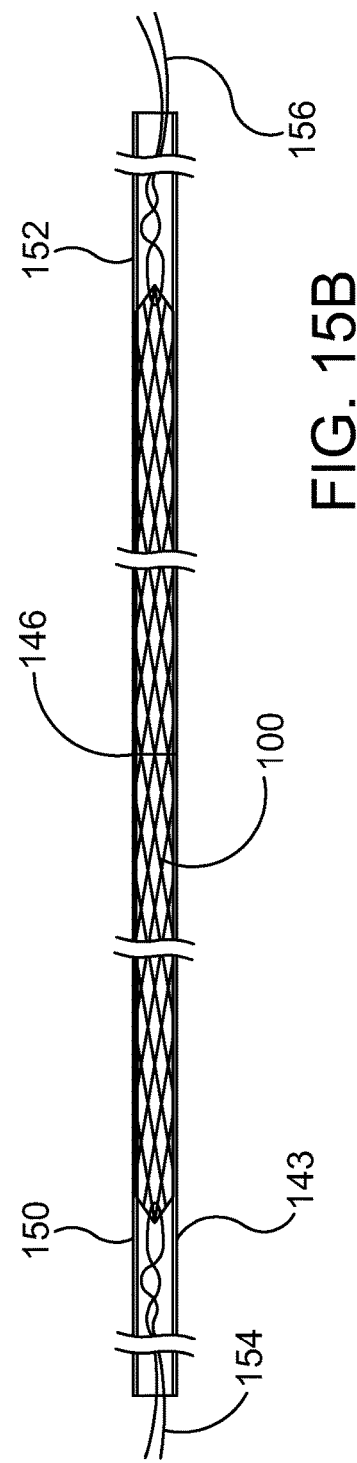

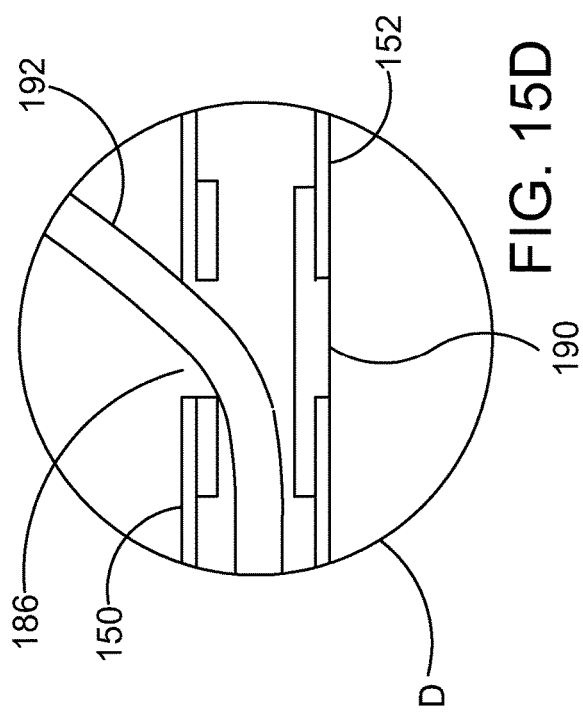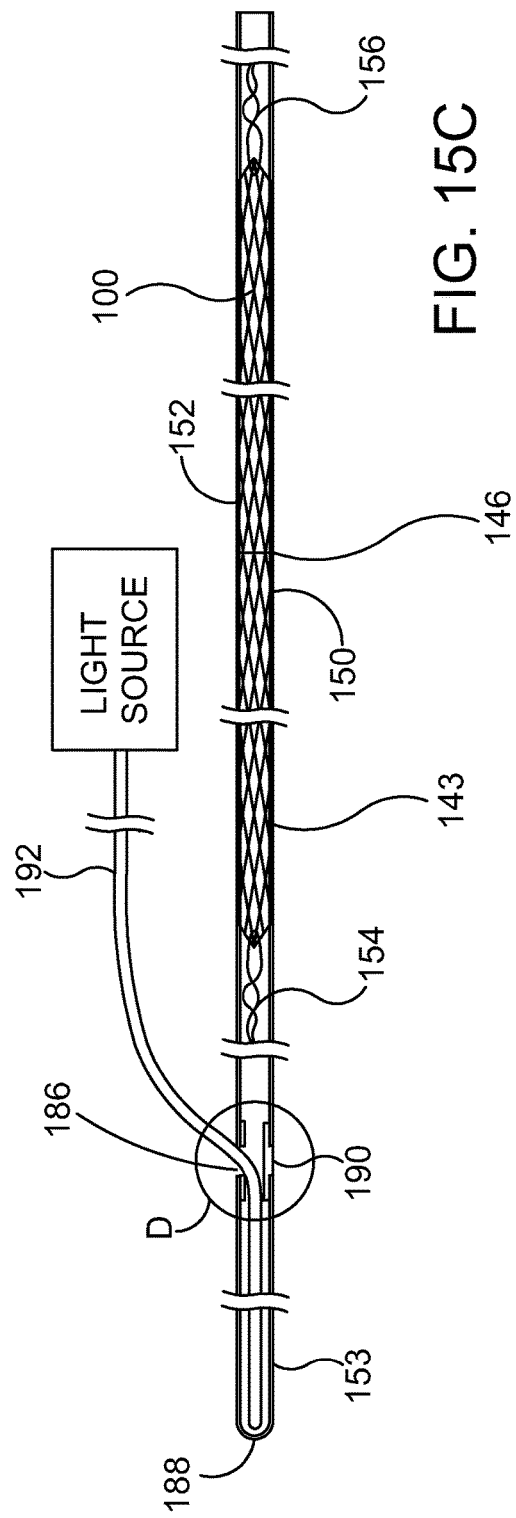

OCULAR IMPLANTS DEPLOYED IN SCHLEMM'S CANAL OF THE EYE

CROSS REFERENCE TO RELATED APPLICATIONS

This application claims the benefit under 35 U.S.C. 119 of U.S. Provisional Patent Application No. 61/357,900, filed Jun. 23, 2010, titled "Ocular Implants Deployed via Biodegradation". This application is herein incorporated by reference in its entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

The present invention relates generally to devices that are implanted within the eye. More particularly, the present invention relates to systems, devices and methods for deploying ocular implants in the eye.

BACKGROUND OF THE INVENTION

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues. If the flow of aqueous humor leaving the eye becomes constricted, pressure begins to build inside the eye.

Aqueous humor is produced by organs known as the ciliary bodies. Each ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried out of the eye by venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," *Investigative Ophthalmology* (February 1966)). Other early glaucoma treatment implants led from the anterior chamber to a sub-conjunctival bleb (e.g., U.S. Pat. Nos. 4,968,296 and 5,180,362). Still others were shunts leading from the anterior chamber to a point just inside Schlemm's canal (Spiegel et al., "Schlemm's canal implant: a new method to lower intraocular pressure in patients with POAG?" *Ophthalmic Surgery and Lasers* (June 1999); U.S. Pat. Nos. 6,450,984; 6,450,984).

SUMMARY OF THE DISCLOSURE

In one embodiment, an ocular implant is provided, comprising an implant body sized and configured to be inserted into Schlemm's canal of an eye, the implant body comprising a plurality of filars, each filar having a proximal end, a distal end and an intermediate portion extending between the proximal end and the distal end, the distal ends of the filars being fixed to each other and the proximal ends of the filars being fixed to each other, the ocular implant being configured to move between a radially collapsed state and a radially expanded state, wherein the ocular implant is configured to assume the radially expanded state when no external forces are acting thereon, and the ocular implant is configured to assume the radially collapsed state when constraining forces are applied to the ocular implant.

In one embodiment, the constraining forces are applied to the intermediate portions of the filars when elongating forces are applied to the proximal and distal portions of the filars. In another embodiment, the constraining forces are applied to the intermediate portions of the filars when the proximal and distal portions of the filars are moved away from each other. In additional embodiments, the constraining forces are applied to the intermediate portions of the filars by a sacrificial material that adheres the individual filars together in a matrix which restricts motion between the individual filars so that expansion of the ocular implant is prohibited.

In some embodiments, the ocular implant has a first pushability when the ocular implant is in the radially expanded state, the ocular implant has a second pushability when the ocular implant is in the radially collapsed state, and the second pushability is greater than the first pushability so as to facilitate advancement of the ocular implant into Schlemm's canal.

In one embodiment, the ocular implant has a first lateral dimension when the ocular implant is in the radially expanded state, the ocular implant has a second lateral dimension when the ocular implant is in the radially collapsed state, and the second lateral dimension is smaller than the first lateral dimension so as to facilitate advancement of the ocular implant into Schlemm's canal.

In some embodiments, a volume defined by the ocular implant has a circular cross-section. In other embodiments, a volume defined by the ocular implant has a non-circular cross-section. In yet another embodiment, a volume defined by the ocular implant has a generally ovoid or elliptical cross-section.

In some embodiments, the intermediate portions of the filars converge toward each other when oppositely directed axial pulling forces are applied to distal and proximal ends of the ocular implant.

In one embodiment, the proximal ends of the filars are fixed to a proximal hub and the distal ends of the filars are fixed to a distal hub.

In additional embodiments each hub comprises a weld bead formed of material from the filars.

In some embodiments, each filar follows a path that curves through three dimensional space as the filar extends distally between the proximal hub and the distal hub.

In one embodiment, constraining forces are applied to the intermediate portions of the filars when elongating forces are applied to the proximal and distal hubs. In another embodiment, constraining forces are applied to the intermediate portions of the filars when the proximal and distal hubs are moved away from each other.

In some embodiments, the path followed by each filar substantially conforms to the shape of a helix.

In one embodiment, the ocular implant further comprises a sacrificial material fixing at least a portion of a body of the ocular implant in the radially collapsed state.

In some embodiments, a proximal portion of the ocular implant is not fixed in the radially collapsed state so as to be free to expand into contact with Schlemm's canal to prevent migration of the ocular implant while the sacrificial material is dissolving.

A method of facilitating fluid flow through the Schlemm's canal of an eye is provided, comprising urging an ocular implant to assume a collapsed state, fixing the ocular implant in the collapsed state, advancing the ocular implant into Schlemm's canal while the ocular implant is fixed in the collapsed state, and allowing the ocular implant to assume an expanded state while at least a portion of the ocular implant is disposed inside Schlemm's canal.

In some embodiments, the step of fixing the ocular implant in the collapsed state comprises applying a sacrificial material to the ocular implant.

In other embodiments, the step of allowing the ocular implant to assume the expanded state comprises allowing the sacrificial material to dissolve inside Schlemm's canal.

In some embodiments, the step of fixing the ocular implant in the collapsed state comprises inserting the ocular implant into a lumen.

An ocular implant is provided, comprising an implant body sized and configured to be inserted into Schlemm's canal of a patient, the implant body comprising a plurality of filars that are interlinked to define a lumen and facilitate the flow of aqueous humor, a sacrificial material disposed on the filars and configured to fix the implant body in a collapsed state, the filars being configured to assume an expanded state when the sacrificial material is removed.

In some embodiments, the sacrificial material comprises a bioabsorbable material configured to dissolve after implantation into Schlemm's canal.

In another embodiment, the filars are pre-biased to expand outwardly.

BRIEF DESCRIPTION OF THE DRAWINGS

FIG. 9 is a plan view of an ocular implant in accordance with the present detailed description.

FIG. 10A and FIG. 10B are stylized plan views illustrating an ocular implant in accordance with this detailed description.

FIG. 10C is a plan view further illustrating the structure of the ocular implant shown in the previous figure. In the embodiment of FIG. 10C, a short section of the ocular implant is shown as though it has been cut along a cutting line parallel to its longitudinal axis and laid out flat. FIG. 10D is an exploded view of the ocular implant section shown in FIG. 10C.

FIGS. 11A-11H are a sequence of stylized plan views illustrating a method in accordance with the present detailed description.

FIGS. 12A-12E are a sequence of stylized plan views illustrating a welding process in accordance with the present detailed description.

FIGS. 13A-13C are a sequence of stylized plan views illustrating a method in accordance with the present detailed description.

FIGS. 15A-15M are a sequence of stylized plan views illustrating a method in accordance with the present detailed description. The method illustrated in FIG. 15 may be used, for example, for assembling a catheter and for placing an ocular implant into Schlemm's canal of an eye using a catheter.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1:
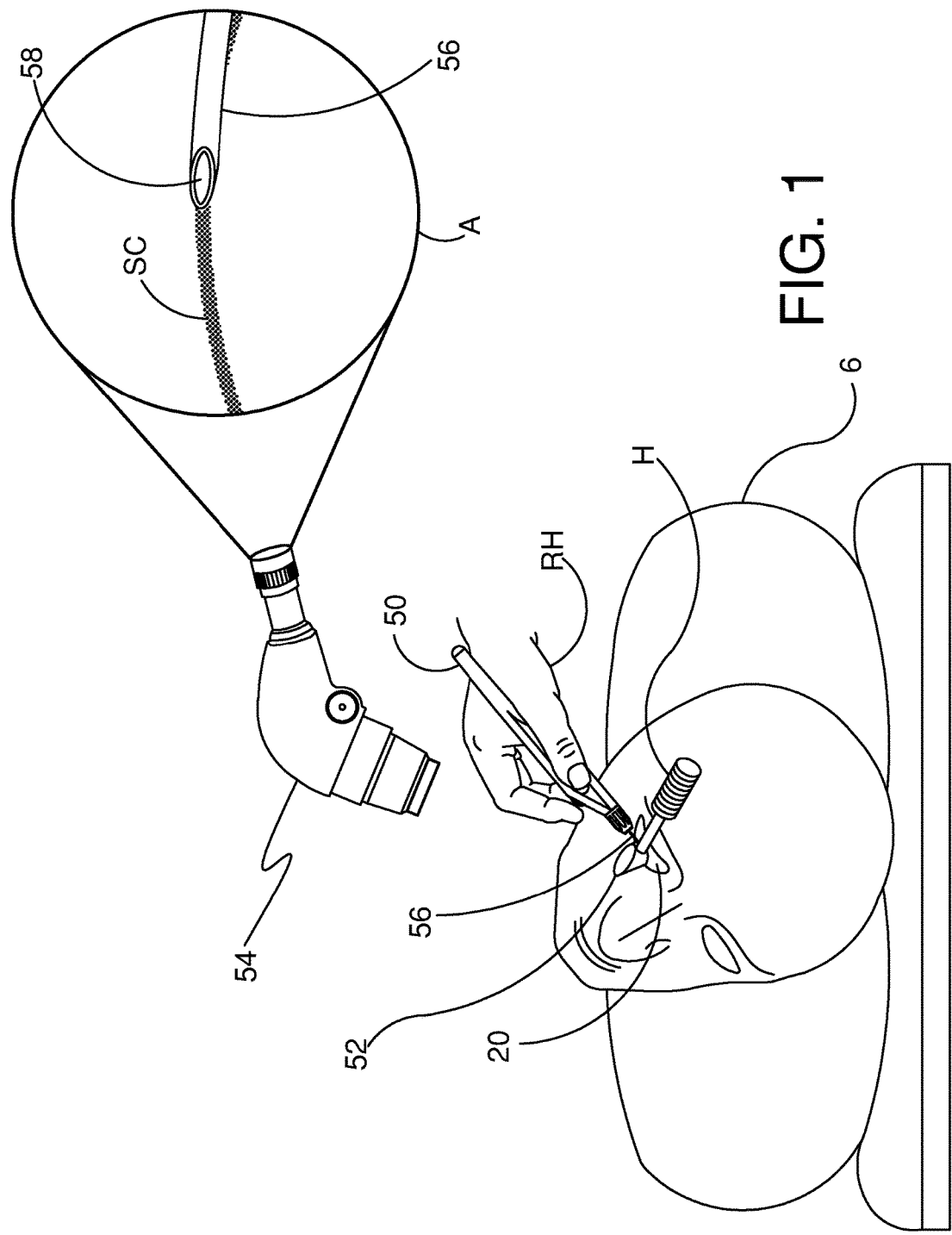
FIG. 1 is a stylized representation of a medical procedure in accordance with this detailed description.

FIG. 1 is stylized representation of a medical procedure in accordance with this detailed description. In the procedure of FIG. 1, a physician is treating an eye 20 of a patient 6. In the procedure of FIG. 1, a physician is holding a hand piece of a delivery system 50 in his or her right hand RH. The physician's left hand (not shown) may be used to hold the handle H of a gonio lens 52. It will be appreciated that some physician's may prefer holding the delivery system handle in the left hand and the gonio lens handle H in the right hand RH.

During the procedure illustrated in FIG. 1, the physician may view the interior of the anterior chamber using a microscope 54 and gonio lens 52. Detail A of FIG. 1 is a stylized simulation of the image viewed by the physician. A distal portion of a cannula 56 is visible in Detail A. A shadow-like line indicates the location of Schlemm's canal SC which is lying under various tissue (e.g., the trabecular meshwork) that surround the anterior chamber. A distal opening 58 of cannula 56 is positioned near Schlemm's canal SC of eye 20.

Methods in accordance with this detailed description may include the step of advancing the distal end of a cannula (e.g., cannula 56 of FIG. 1) through the cornea of eye 20 so that a distal portion of the cannula is disposed in the anterior chamber of the eye. Cannula 56 may then be used to access Schlemm's canal of the eye, for example, by piercing the wall of Schlemm's canal with the distal end of cannula 56. Distal opening 58 of cannula 56 may be placed in fluid communication with a lumen defined by Schlemm's canal. The ocular implant may be advanced out of distal opening 58 and into Schlemm's canal. Insertion of the ocular implant into Schlemm's canal may facilitate the flow of aqueous humor out of the anterior chamber of the eye.

Figure 2:
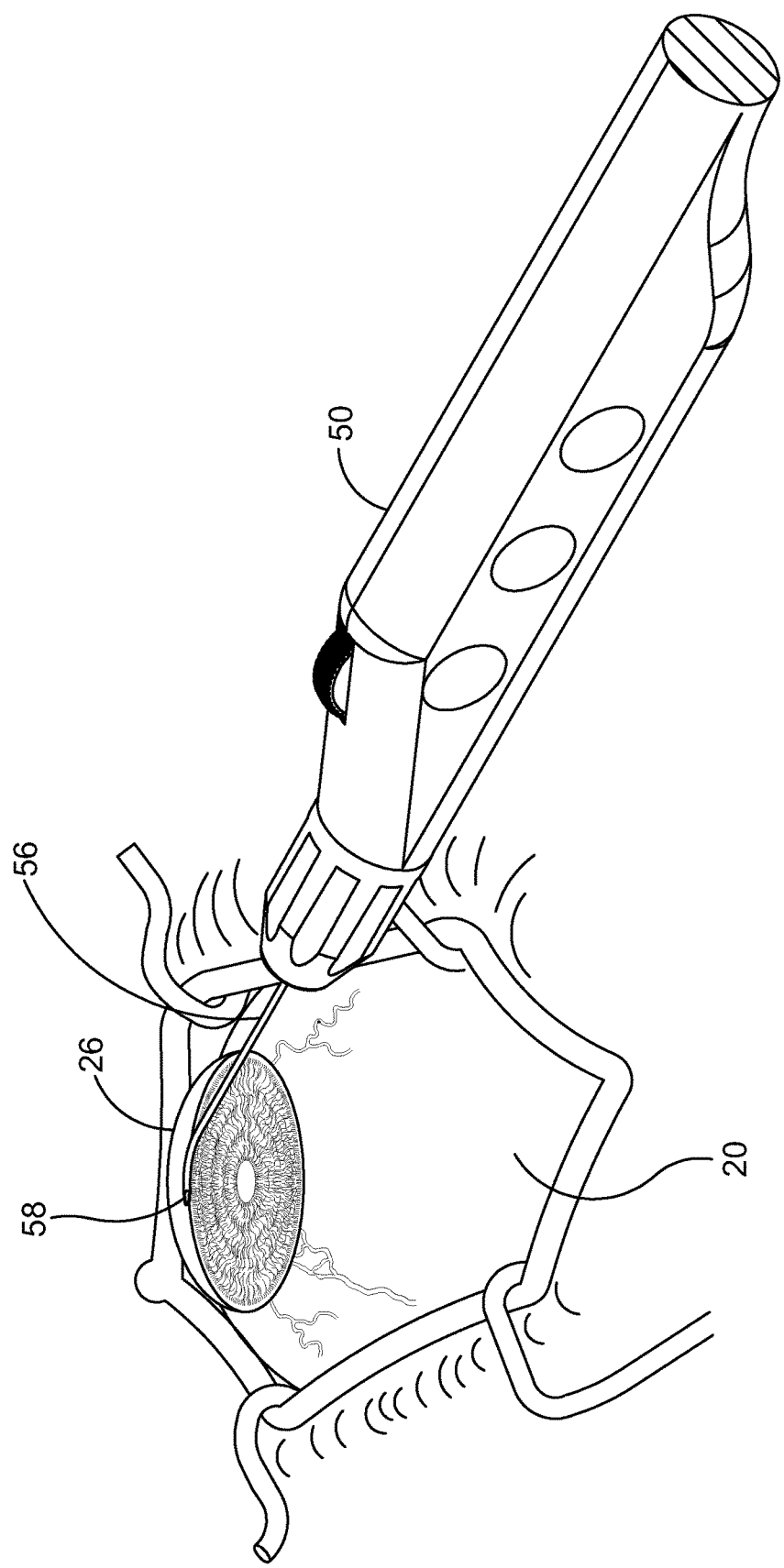
FIG. 2 is an enlarged perspective view further illustrating the delivery system hand piece and the eye shown in the previous figure.

FIG. 2 is an enlarged perspective view further illustrating delivery system 50 and eye 20 shown in the previous figure. In FIG. 2, cannula 56 of delivery system 50 is shown extending through a cornea 26 of eye 20. A distal portion of cannula 56 is disposed inside the anterior chamber defined by cornea 26 of eye 20. In the embodiment of FIG. 2, cannula 56 is configured so that a distal opening 58 of cannula 56 can be placed in fluid communication with Schlemm's canal.

In the embodiment of FIG. 2, an ocular implant is disposed in a passageway defined by cannula 56. Delivery system 50 includes a mechanism that is capable of advancing and retracting the ocular implant along the length of cannula 56. The ocular implant may be placed in Schlemm's canal of eye 20 by advancing the ocular implant through the distal opening of cannula 56 while the distal opening is in fluid communication with Schlemm's canal.

Figure 3:
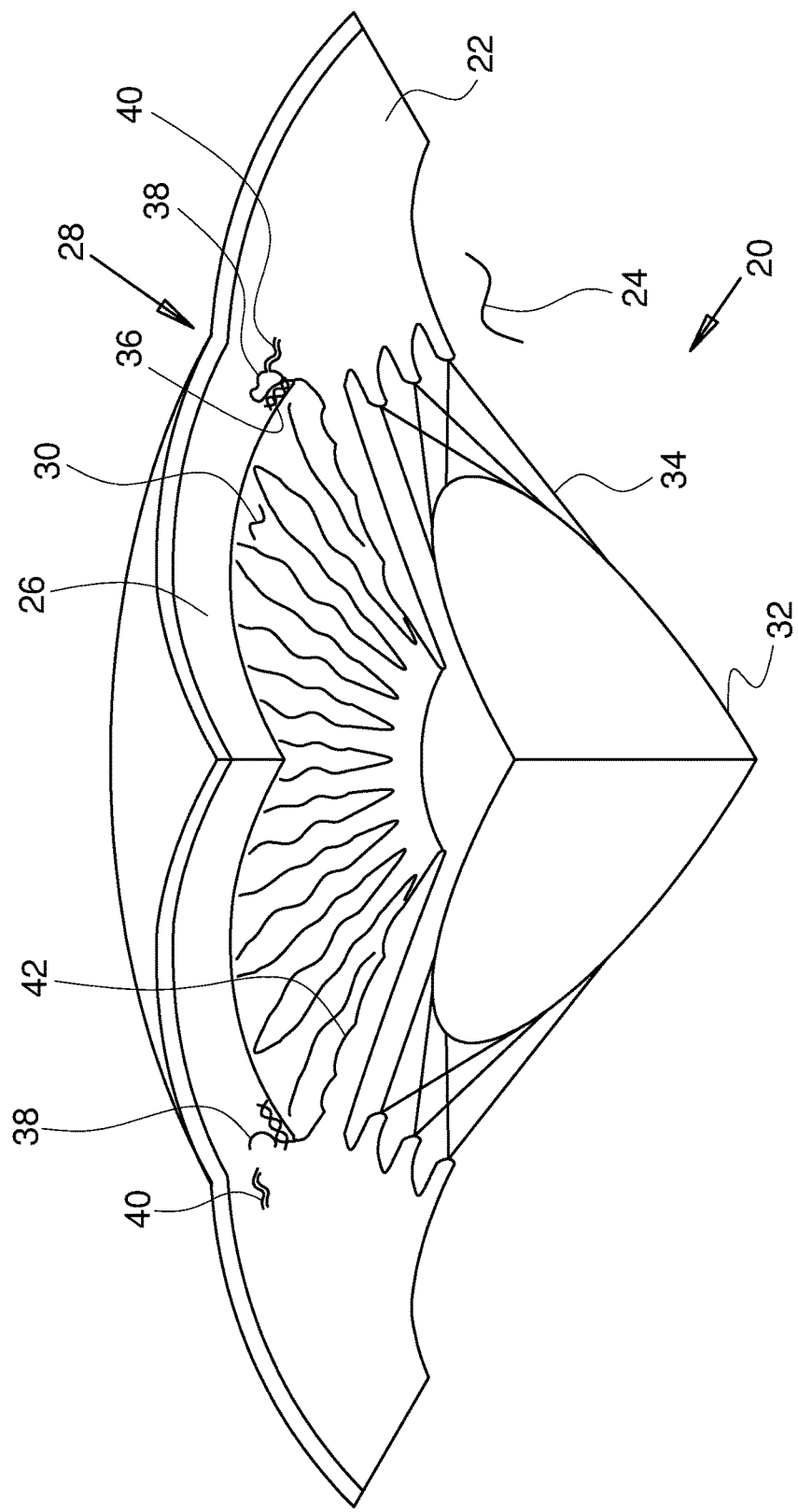
FIG. 3 is a stylized perspective view illustrating a portion of the eye shown in the previous figure.

FIG. 3 is a stylized perspective view illustrating a portion of eye 20 shown in the previous figure. Eye 20 can be conceptualized as a fluid filled ball having two chambers. Sclera 22 of eye 20 surrounds a posterior chamber 24 filled with a viscous fluid known as vitreous humor. Cornea 26 of eye 20 encloses an anterior chamber AC that is filled with a fluid known as aqueous humor. The cornea 26 meets the sclera 22 at a limbus 28 of eye 20. A lens 32 of eye 20 is located between anterior chamber AC and posterior chamber 24. Lens 32 is held in place by a number of ciliary zonules 34.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

In a healthy eye, aqueous humor flows out of the anterior chamber AC through the trabecular meshwork TM and into Schlemm's canal SC, located at the outer edge of the iris 42. Aqueous humor exits Schlemm's canal SC and flows into a number of collector channels 40. After leaving Schlemm's canal SC, aqueous humor is absorbed into the venous blood stream.

Figure 4:
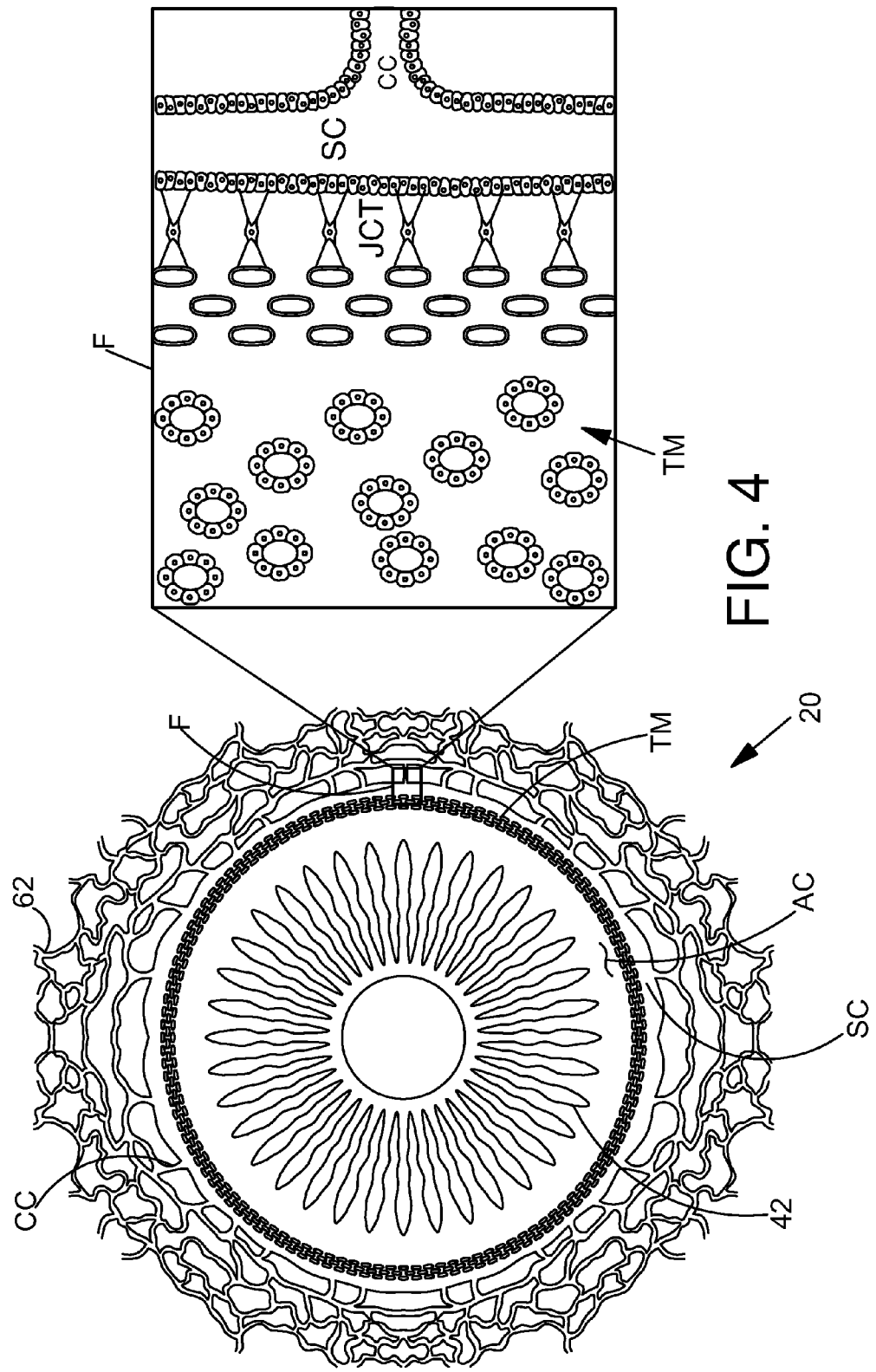
FIG. 4 is an anterior plan view of the eye shown in the previous figure.

FIG. 4 is an anterior plan view of eye 20 shown in the previous figure. In FIG. 4, Schlemm's canal SC can be seen encircling iris 42. Aqueous humor exits anterior chamber AC and enters Schlemm's canal SC by flowing through the trabecular meshwork TM. Aqueous humor exits Schlemm's canal SC by flowing through a number of collector channels CC. After leaving Schlemm's canal SC, aqueous humor travels through veins 62 and is absorbed into the blood stream. Schlemm's canal typically has a non-circular cross-sectional shape whose diameter can vary along the canal's length and according to the angle at which the diameter is measured. In addition, there may be multiple partial pockets or partial compartments (not shown in these figures) formed along the length of Schlemm's canal. The shape and diameter of portions of Schlemm's canal and the existence and relative location of partial pockets or compartments may limit or prevent fluid flow from one point of Schlemm's canal to another. Hence, each collector channel CC from Schlemm's canal may drain only a portion of Schlemm's canal. For purposes of illustration, a portion of eye 20 is surrounded by a frame F in FIG. 4. This portion of eye 20 is enlarged for purposes of illustration in FIGS. 4.

Figure 5:
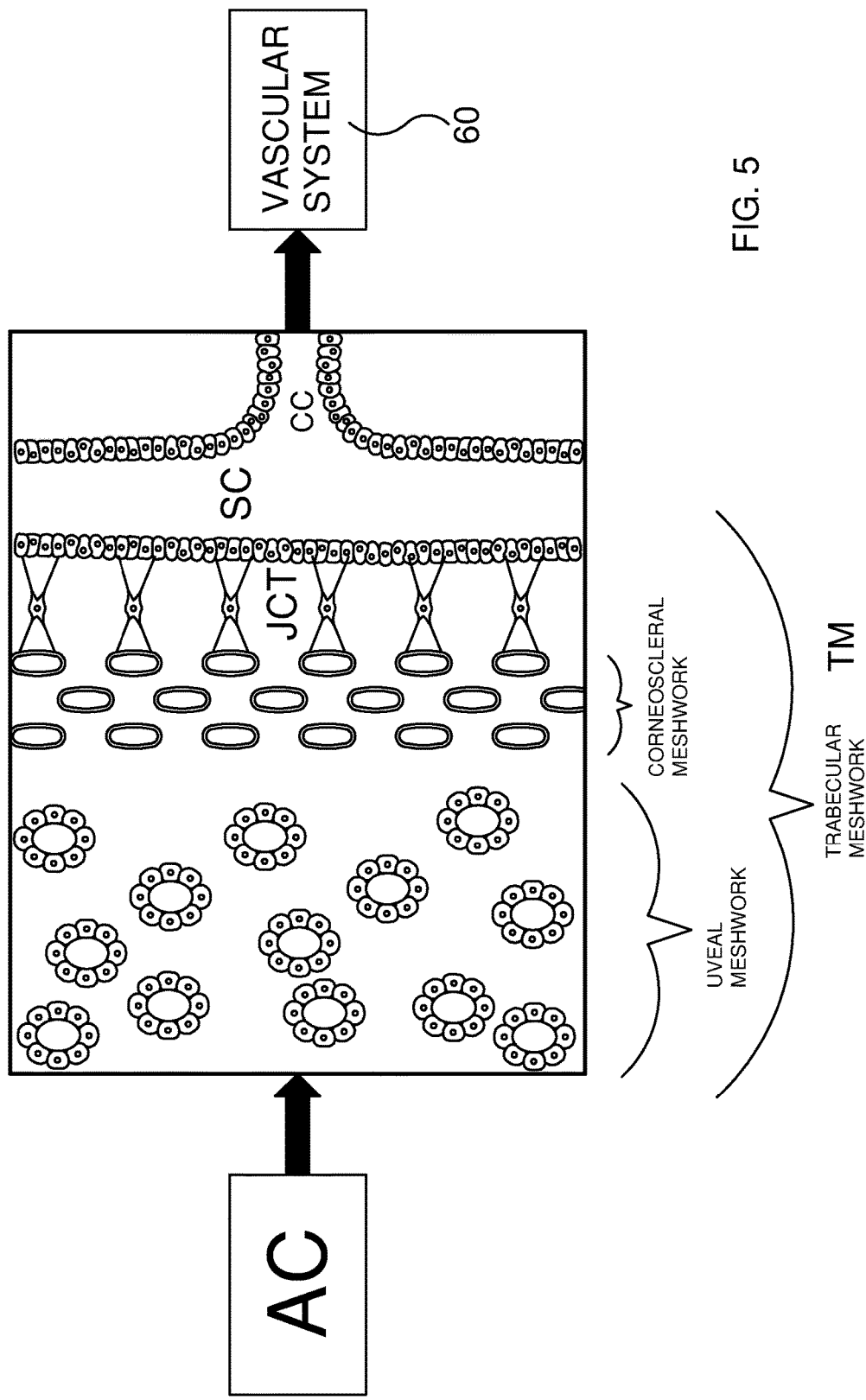
FIG. 5 is a stylized diagram illustrating the flow of aqueous humor out of the anterior chamber of the eye and into the vascular system of the body.

FIG. 5 is a stylized diagram illustrating the flow of aqueous humor out of the anterior chamber AC and into the vascular system 60. Aqueous humor enters Schlemm's canal SC by flowing out of the anterior chamber AC, through trabecular meshwork TM, and through the wall of Schlemm's canal SC. Aqueous humor exits Schlemm's canal SC and flows into a number of collector channels CC. One collector channel CC is shown in FIG. 5. After leaving Schlemm's canal SC, aqueous humor is absorbed into venous blood in the vascular system 60.

Figure 6:
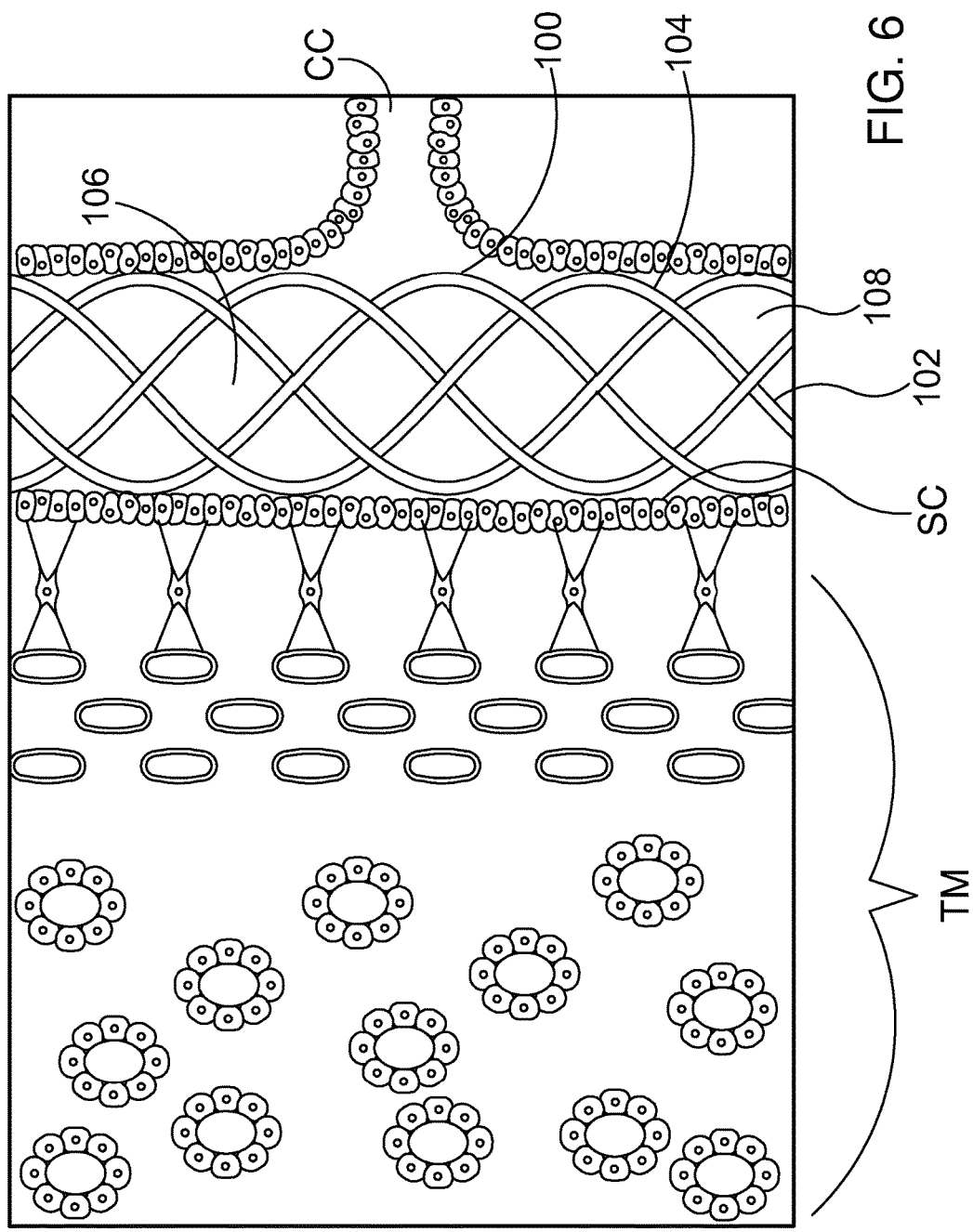
FIG. 6 is a stylized diagram showing Schlemm's canal, a collector channel and trabecular meshwork of an eye with an active implant in its expanded state.

FIG. 6 is a stylized diagram showing Schlemm's canal SC, collector channel CC, and trabecular meshwork TM. In FIG. 6, an ocular implant 100 is disposed in Schlemm's canal SC. In the embodiment of FIG. 6, ocular implant 100 comprises a plurality of filars 102 forming a body 104. Body 104 of ocular implant 100 defines a lumen 106 and plurality of interstitial spaces 108 fluidly communicating with lumen 106.

Ocular implant 100 may be inserted into Schlemm's canal of a human eye to facilitate the flow of aqueous humor out of the anterior chamber. This flow may include axial flow along Schlemm's canal, flow from the anterior chamber into Schlemm's canal, and flow leaving Schlemm's canal via a plurality of collector channels CC. When in place within the eye, ocular implant 100 will support trabecular mesh tissue and Schlemm's canal tissue and will provide for improved communication between the anterior chamber and Schlemm's canal (via the trabecular meshwork) and between pockets or compartments along Schlemm's canal.

Filars 102 of ocular implant 100 may be interlinked with one another to form body 104. When this is the case, various processes may be used to interlink the filars with one another. Examples of processes that may be suitable in some applications including braiding, weaving, and knitting.

In FIG. 6, ocular implant 100 is shown assuming an expanded state. In some useful methods, ocular implant 100 is allowed to assume the expanded state while the ocular implant is residing in Schlemm's canal. The presence of the expanded state ocular implant in Schlemm's canal may facilitate the flow of aqueous humor out of the anterior chamber. Ocular implant 100 is also capable of assuming a radially collapsed state. The ocular implant may have a relatively low profile shape when it is in the radially contracted shape. This low profile shape may minimize any trauma incurred by eye tissues during the delivery procedure. The low profile shape may also enable the delivery of ocular implants having greater length than would otherwise be possible. Some methods in accordance with this detailed description may include the step of urging an ocular implant to assume the collapsed state prior to advancing the ocular implant into Schlemm's canal. A sacrificial material may be added to the ocular implant so that the ocular implant is fixed in the collapsed state. In some useful methods, ocular implant 100 is advanced into Schlemm's canal SC while ocular implant 100 is fixed in the collapsed state. Ocular implant 100 may be allowed to assume the expanded state while at least a portion of ocular implant 100 is disposed inside Schlemm's canal.

In some useful embodiments, the sacrificial material comprises a bioabsorbable material (e.g., a biodegradable polymer). A biodegradable polymer may be used to capture and retain the filars of the ocular implant in its radially collapsed/longitudinally stretched configuration. The ocular implant may be delivered into Schlemm's canal while the ocular implant is assuming its radially collapsed/longitudinally stretched configuration. Over time, the biodegradable polymer dissolves and the retaining force previously holding the implant in the low profile state is eliminated. This allows the ocular implant to assume a higher profile state. The biodegradable material could be a polymer used strictly as a fixation means or alternatively a therapeutic agent and/or a lubricant could be added to the base material. The biodegradable material can be applied to the material by a variety of methods including spraying, dipping, extrusion and reflow extrusion. The biodegradable material can be applied to the entire length of the implant or can be placed at predefined locations as needed.

Figure 7:
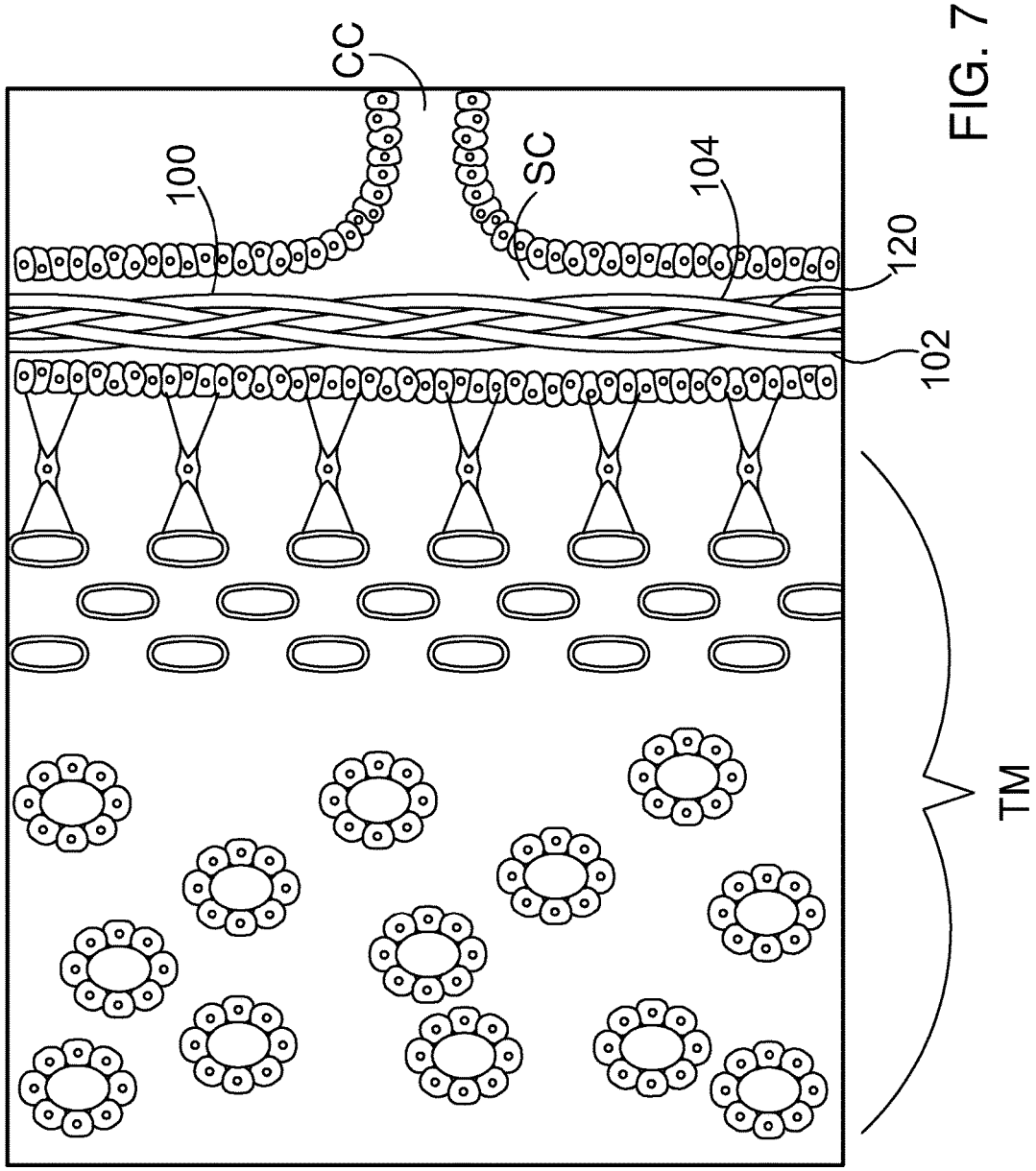
FIG. 7 is an additional stylized diagram showing Schlemm's canal SC and an ocular implant in its compressed state.

FIG. 7 is an additional stylized diagram showing Schlemm's canal SC and ocular implant 100. In FIG. 7, ocular implant 100 is shown assuming a collapsed state. Ocular implant 100 is also capable of assuming the expanded state shown in the previous figure. In the embodiment of FIG. 7, ocular implant 100 is fixed in the collapsed state by a sacrificial material 120 that adheres the individual filars 102 together in a matrix which restricts motion between the individual filars which in turn restricts expansion.

With reference to FIG. 7, it will be appreciated that ocular implant 100 has been advanced into Schlemm's canal SC while ocular implant 100 is fixed in the collapsed state. Ocular implant 100 may be allowed to assume the expanded state while at least a portion of ocular implant 100 is disposed inside Schlemm's canal. In the embodiment of FIG. 7, sacrificial material 120 is adapted to erode over time. As sacrificial material 120 erodes, the retaining force holding the implant in the collapsed state is eliminated. This allows the ocular implant to assume an expanded state.

With reference to FIG. 7, it will be appreciated that ocular implant 100 comprises a plurality of filars forming a body 104. Body 104 defines a lumen and a plurality of interstitial spaces that fluidly communicate with the lumen. In the embodiment of FIG. 7, body 104 is biased to assume an expanded state when filars 102 are in the least stressed condition (i.e. the filars may still be stress in the expanded state but they are at the lowest stress that the structure can achieve). A sacrificial material 120 overlays and surrounds the filar matrix. Sacrificial material 120 is fixing body 104 in the collapsed state in the embodiment of FIG. 7. In the embodiment of FIG. 7, filars 102 are in intimate contact with each other such that the lumen and interstitial spaces defined by the filars 102 are very small and/or completely closed. By comparing FIG. 7 and FIG. 6, it will be appreciated that ocular implant 100 has a relatively low profile when the lumen and interstitial spaces defined by the filars 102 are very small and/or completely closed. The low profile of the ocular implant may facilitate delivery of the ocular implant into Schlemm's canal. The low profile of the ocular implant may also minimize any trauma incurred by eye tissues during the delivery procedure. The low profile of the ocular implant may also enable the delivery of ocular implants having greater length than would otherwise be possible.

Figure 8:
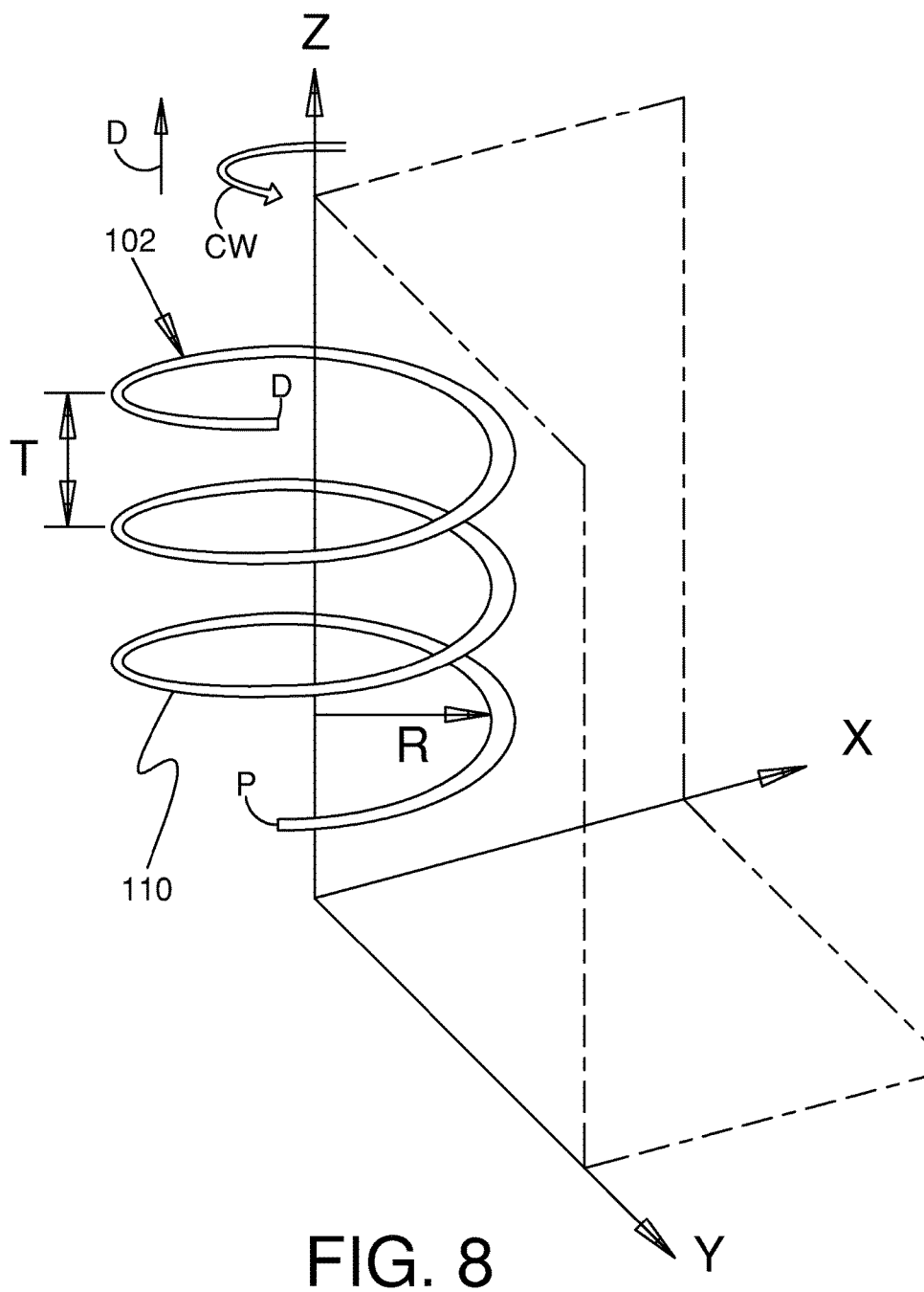
FIG. 8 is a perspective view showing an illustrative filar.

In one embodiment, an ocular implant may include a plurality of filars; each filar following a path that curves in three dimensions. The filars may be interlinked to form a body defining a lumen. FIG. 8 is a perspective view showing an illustrative filar 102. With reference to FIG. 8, it will be appreciated that filar 102 extends through three mutually orthogonal planes: a first plane xy, a second plane xz, and a third plane yz. First plane xy is defined by an X-axis and a Y-axis. Second plane xz is defined by the X-axis and a Z-axis. Third plane yz is defined by the Y-axis and the Z-axis.

Filar 102 includes a number of turns 110 that wrap loosely about the Z-axis shown in FIG. 8. With reference to FIG. 8, it will be appreciated that filar 102 does not lie completely on any one of the three planes shown in FIG. 8 (i.e., first plane xy, second plane xz, and third plane yz). Filar 102 has a proximal end P, a distal end D, and an intermediate portion that extends between the proximal end and the distal end. With reference to FIG. 8, it will be appreciated that filar 102 spirals in a clockwise direction CW as it extends distally from proximal end P to distal end D. However, in other embodiments, the filar can spiral in the counterclockwise direction CCW as it extends distally from proximal end P to distal end D.

In the embodiment of FIG. 8, filar 102 has a pitch T. Pitch T may be defined as the distance between the centers of adjacent turns 110 of filar 102. In the embodiment of FIG. 8, pitch T is constant along the length of filar 102. Also in the embodiment of FIG. 8, filar 102 has a radius R that is substantially constant throughout the rotation of filar 102. In the embodiment of FIG. 8, it will be appreciated that filar 102 forms a helix. It will also be appreciated, however, that some three dimensionally shaped curves do not form helices. Additionally, it will be appreciated that three dimensionally shaped curves are possible which have a radius that varies through the rotation of the three dimensionally shaped curve unlike filar 102 shown in FIG. 8. In the embodiment of FIG. 8, filar 102 completes three complete revolutions. Each of these revolutions has an angular span of three hundred and sixty degrees.

FIG. 9 is a plan view of an ocular implant in accordance with the present detailed description. In the embodiment of FIG. 9, ocular implant 100 comprises a plurality of filars 102 forming a body 104. In the embodiment of FIG. 9, ocular implant 100 comprises eight filars that are interlinked with one another to form body 104. In other embodiments, any number of filars can be used in the ocular implant. In some useful embodiments, the ocular implant has an even number of filars. Fabricating the ocular implant with a plurality of filars has many benefits. For example, a filar style ocular implant uses a minimal amount of material compared to a tubular implant, so an implant to aqueous flow volume is maximized. Additionally, an ocular implant constructed from a plurality of filars is more forgiving to flexing and bending than conventional ocular implants. In the embodiment of FIG. 9, a distal end of each filar is fixed to a distal hub 124 and a proximal end of each filar is fixed to a proximal hub 122. The eight filars of ocular implant 100 may be conceptually divided into two sets; set A and set B. Each filar in set A spirals in a clockwise direction CW as it extends distally away from proximal hub 122. The distal direction is illustrated with an arrow D in FIG. 9. Each filar in set B spirals in a counterclockwise direction CCW as it extends distally away from proximal hub 122.

In the embodiment of FIG. 9, each filar in set A follows a generally helical path alternately crossing over and under filars in set B. The generally helical path of each filar and criss-crossing nature of the implant forms a strong, resilient structure. Similarly, each filar in set B follows a generally helical path alternately crossing over and under filars in set A. It should be noted that the radius of the helical path of each individual filar may become slightly larger and then smaller repeatedly as the filar crosses over and under neighboring filars. The path of each filar may conform to a number of logical rules in the embodiment of FIG. 9. First, a filar in one set does not cross a filar in its own set. Second, each filar alternates crossing over and under filars in the other set. Third, the order that each filar crosses the filars in the other set is the same and is repetitive. Fourth, each filar does not cross any filar in the other set a second time before crossing each filar in the other set a first time.

Filars 102 of ocular implant 100 may comprise various materials without deviating from the spirit and scope of the present invention. One particularly useful material is known as drawn filled tube (DFT). Drawn filled tube can be commercially available from Fort Wayne Metals of Fort Wayne, Pa. (e.g., Pt-DFT®-95% Niti). The drawn filled tube may comprise a core of 95% Nitinol and an outer sheath of platinum. The outer sheath of platinum may advantageously prevent oxides from forming on the nitinol core, for example, during heat treating processes. In one useful embodiment, each filar comprises a wire having a circular cross-sectional shape and an outer diameter of about is 0.00075 inch. Other potential high strength biocompatible alloys with suitable spring properties include 316 stainless steel, Elgiloy, MP-35N, and bio absorbable Magnesium.

FIG. 10A and FIG. 10B are stylized plan views illustrating one embodiment of an ocular implant 100 in accordance with this detailed description. In FIG. 10A, ocular implant 100 is shown in a radially expanded state. In FIG. 10B, ocular implant 100 is shown in a radially collapsed state. In one embodiment, the ocular implant has a radius of approximately 0.025-0.030 cm in the expanded state, and has a radius of approximately 0.01-0.015 cm in the collapsed state. FIG. 10A and FIG. 10B may be collectively referred to as FIG. 10.

In the embodiment of FIG. 10, ocular implant 100 comprises a plurality of filars 102 forming a body 104. Body 104 of ocular implant 100 defines a lumen 106 and plurality of interstitial spaces 108 fluidly communicating with lumen 106. The filars 102 of ocular implant 100 are interlinked with one another to form body 104.

Ocular implant 100 of FIG. 10 comprises eight filars. A distal end of each filar is fixed to a distal hub 124 and a proximal end of each filar is fixed to a proximal hub 122. The eight filars of ocular implant 100 may be conceptually divided into two sets; set A and set B. Each filar in set A spirals in a clockwise direction CW as it extends distally away from proximal hub 122. The distal direction is illustrated with an arrow D in FIG. 10. Each filar in set B spirals in a counterclockwise direction CCW as it extends distally away from proximal hub 122. In other embodiments, the ocular implant can include any number of filars, including more or less than eight filars.

In the embodiment of FIG. 10, each filar in set A follows a generally helical path alternately crossing over and under filars in set B. Similarly, each filar in set B follows a generally helical path alternately crossing over and under filars in set A. It should be noted that the radius of the helical path of each individual filar may be come slightly larger and then smaller repeatedly as the filar crosses over and under neighboring filars. The path of each filar conforms to a number of logical rules in the embodiment of FIG. 10. First, a filar in one set does not cross a filar in its own set. Second, each filar alternates crossing over and under filars in the other set. Third, the order that each filar crosses the filars in the other set is the same and is repetitive. Fourth, each filar does not cross any filar in the other set a second time before crossing each filar in the other set a first time.

Filars 102 of ocular implant 100 can be spring biased outward, so that filars 102 exert an outward force on the walls of Schlemm's canal. Migration of the ocular implant is made less likely when the filars of the ocular implant engage the walls of Schlemm's canal with these outwardly directed spring forces. An angle A is illustrated using dimension lines in FIG. 10. In FIG. 10, angle A represents an angle defined between a filar from set A and a filar from set B. In some useful embodiments, the cross angle of the individual filars when the implant is expanded is about ninety degrees. At this angle the area (and fluid flow path) between the filars is at a maximum, which allows the implant to provide the maximum amount of flow for aqueous humor. As described previously, each filar of an ocular implant may follow a three dimensionally shaped curving path. In the embodiment of FIG. 10, the shape of filars 102 will cause them to travel across the wall of Schlemm's canal at an angle relative to the longitudinal axis of the ocular implant. The cross-ways engagement of the filars with the wall of Schlemm's canal can be appreciated by observing the cross-ways path of the filars seen in FIG. 10A. The cross-ways engagement of the filars with the wall of Schlemm's canal may prevent the ocular implant from migrating. The three dimensionally shaped curving path of the filars also causes the filars to be easily compressible in a direction parallel to the longitudinal axis of the ocular implant. This longitudinal compressibility of the filars may also make migration of the ocular implant less likely.

The filars provide support for the walls of Schlemm's canal and the trabecular meshwork that overlays the inner major wall of Schlemm's canal. Filars 102 of ocular implant 100 can be spring biased outward, so that filars 102 exert an outward force on the walls of Schlemm's canal. The outward force applied to the walls of Schlemm's canal helps prevent ocular implant 100 from leaving its desired position. In some useful embodiments, the ocular implant may stretch the trabecular meshwork and the walls of Schlemm's canal in a way that makes the trabecular meshwork more permeable. Making the trabecular meshwork more permeable may facilitate the flow of aqueous humor out of the anterior chamber.

In FIG. 10B, ocular implant 100 is shown in a radially collapsed state. Ocular implant 100 is configured to assume the radially collapsed state shown in FIG. 10B when elongating forces are applied to the proximal and distal hubs. By comparing FIG. 10A and FIG. 10B, it will be appreciated that the intermediate portions of filars 102 move toward each other when ocular implant 100 is urged to assume the radially collapsed state. In the embodiment of FIG. 10, the pushability of ocular implant 100 is increased when ocular implant 100 is urged to assume the radially collapsed state. Pushability generally concerns the ability of an ocular implant to transmit to the distal end of the ocular implant an axial force applied to the proximal end of the ocular implant. Also in the embodiment of FIG. 10, the outer dimensions of ocular implant 100 decrease when ocular implant 100 is urged to assume the radially collapsed state. Delivery of ocular implant 100 is facilitated by urging the ocular implant to assume a state having a low profile shape and increased pushability. Advancing the ocular implant into Schlemm's canal while it is in the radially collapsed state may minimize any trauma incurred by eye tissues during the delivery procedure. Advancing the ocular implant into Schlemm's canal while it is in the radially collapsed state may also enable the delivery of ocular implants having greater length than would otherwise be possible. In the embodiment of FIG. 10B, ocular implant 100 can be fixed in the collapsed state by a sacrificial material 120 that adheres the individual filars 102 together in a matrix which restricts motion between the individual filars which in turn restricts expansion. Ocular implant 100 may be allowed to assume the expanded state while at least a portion of ocular implant 100 is disposed inside Schlemm's canal. In the embodiment of FIG. 10B, sacrificial material 120 is adapted to erode over time. As sacrificial material 120 erodes, the retaining force holding the implant in the collapsed state is eliminated. This allows the ocular implant to assume the radially expanded state shown in FIG. 10A.

Sacrificial material 120 may comprise various materials without deviating from the spirit and scope of this detailed description. In some useful embodiments, the sacrificial material comprises a bioabsorbable material (e.g., a biodegradable polymer). Examples of materials that may be suitable in some applications include polycaprolactone, polylactic acid, polyglycolic acid, polylactide coglycolide, polyglactin, poly-L-lactide, polyhydroxalkanoates, starch, and cellulose. Various methods may be used to apply sacrificial material 120 to ocular implant 120. For example, a preform comprising a thermoplastic polymeric material may be placed inside the ocular implant while the ocular implant is in the radially expanded state. The ocular implant may then be urged to assume the radially collapsed state while external heat is applied to reflow the thermoplastic polymeric material of the preform. By way of a second example, the sacrificial material may be sprayed onto the filars. In some embodiments, the sacrificial material may be applied to less than all of the ocular implant. When this is the case, the portion of the ocular implant that is free of the sacrificial material will be free to assume the radially expanded shape. The portion of the ocular implant that is free to assume the radially expanded shape may function to anchor the ocular implant at a desired location while the sacrificial material erodes.

FIG. 10C is a plan view further illustrating the structure of ocular implant 100 shown in the previous figure. In the embodiment of FIG. 10, a short section of ocular implant 100 is shown as though it has been cut along a cutting line parallel to its longitudinal axis and laid out flat. The filars of ocular implant 100 are laid out flat in FIG. 10C to better illustrate the interlinking arrangement of these filars.

FIG. 10D is an exploded view of the portion of ocular implant 100 shown in FIG. 10C. Ocular implant 100 of FIG. 10 comprises eight filars. In other embodiments, however, any number of filars can be included in the ocular implant. In the exploded view of FIG. 10D, the eight filars of ocular implant 100 are physically divided into two sets; set A and set B. In the embodiment of FIG. 10, set A includes a first filar 1A, a second filar 2A, a third filar 3A, and a fourth filar 4A. Set B includes a first filar 1B, a second filar 2B, a third filar 3B, and a fourth filar 4B. In the embodiment of FIG. 10.

In the embodiment of FIG. 10C, each filar in set A follows a generally helical path alternately crossing over and under filars in set B. Similarly, each filar in set B follows a generally helical path alternately crossing over and under filars in set A. Referring still to FIG. 10C, the path of first filar 1A may be described as spiraling in a counter-clockwise direction as the filar extends in a distal direction crossing under first filar 1B, over second filar 2B, under third filar 3B, and over fourth filar 4B. The distal direction is illustrated using an arrow D in FIG. 10A. The path of second filar 2A may be described as spiraling in a counter-clockwise direction as the filar extends in the distal direction crossing over first filar 1B, under second filar 2B, over third filar 3B, and under fourth filar 4B. The path of third filar 3A may be described as spiraling in a counter-clockwise direction as the filar extends in a distal direction crossing under first filar 1B, over second filar 2B, under third filar 3B, and over fourth filar 4B. The path of fourth filar 4A may be described as spiraling in a counter-clockwise direction as the filar extends in the distal direction crossing over first filar 1B, under second filar 2B, over third filar 3B, and under fourth filar 4B.

The paths of the filars in set B may be described in a similar fashion. The path of first filar 1B spirals in a clockwise direction as the filar extends in a distal direction crossing over first filar 1A, under second filar 2A, over third filar 3A, and under fourth filar 4A. The path of second filar 2B spirals in a clockwise direction as the filar extends in the distal direction crossing under first filar 1A, over second filar 2A, under third filar 3A, and over fourth filar 4A. The path of third filar 3B spirals in a clockwise direction as the filar extends in a distal direction crossing over first filar 1A, under second filar 2A, over third filar 3A, and under fourth filar 4A. The path of fourth filar 4B spirals in a clockwise direction as the filar extends in the distal direction crossing under first filar 1A, over second filar 2A, under third filar 3A, and over fourth filar 4A.

FIG. 11A-FIG. 11H are a sequence of stylized plan views illustrating a method in accordance with the present detailed description. FIGS. 11A-11H may be collectively referred to as FIG. 11. The method illustrated in FIG. 11 may be used, for example, form the ocular implant described above.

At FIG. 11A, a plurality of filars are arranged to form an elongate filar structure. At FIG. 11B, a portion of the elongate filar structure is stretched length-wise until the filar structure becomes taut and the smallest profile is achieved. At FIG. 11C, a fixative (e.g., adhesive, solder etc.) is applied to a distal section of the filar structure while it is pulled taut and assuming a low profile shape. The fixative is forced into the filar structure matrix so as to bond the filars together forming a distal tip. The fixative is represented with a pattern of dots in FIG. 11C.

At FIG. 11D, the longitudinal tension on the filar structure is released. With reference to FIG. 11D, it will be appreciated that the low profile tip portion of the filar structure has not expanded. The remainder of the filar structure is shown in an expanded condition in FIG. 11D.

At FIG. 11E, a sleeve has been positioned near the low profile tip portion of the filar structure. In some useful embodiments, the sleeve is made of a material that is brittle and has a higher melting temperature than the braid. Examples of materials that may be suitable include sapphire and fused silca.

At FIG. 11F, the low profile tip section is threaded through the sleeve, tension is applied to the distal end that is exposed allowing the sleeve to be advanced over the filar structure. In some useful embodiments, a lumen defined by the sleeve is configured so that the sleeve captures the filar structure and keeps filars in intimate contact with each other.

At FIG. 11G, the first sleeve has been advanced further along the length of the filar structure. Also in FIG. 11G, a second sleeve has been threaded onto the filar structure. The filar structure can be made having various lengths and sleeves can be advanced over the entire length of filar structure. Accordingly, any number of sleeves can be threaded onto the filar structure. At FIG. 11H, the filar structure is trimmed flush with the ends of the sleeves, for example by laser cutting. The resulting work pieces each comprise a portion of filar structure trapped in a sleeve with filars in intimate contact with each other. Holding the filars in intimate contact with each other advantageously helps to ensure a reliable weld.

FIG. 12A-FIG. 12E are a sequence of stylized plan views illustrating an welding process in accordance with the present detailed description. At FIG. 12A, a workpiece is provided. The workpiece comprises a filar structure that is trapped in a sleeve. In some useful embodiments, a lumen defined by the sleeve is configured so that the sleeve captures the filar structure and keeps filars in intimate contact with each other.

At FIG. 12B, a proximal end of the filar structure is exposed to laser or other welding energy. The laser energy is sufficient to melt the filars and fuse them to each other. The laser energy is not sufficient to melt the sleeve encasing the filar structure. The sleeve effectively creates a mold to maintain the outer diameter of the welded zone/molten metal of the filars. An energy profile is selected that causes the material to assume a semi-circular profile when solidified which provides a desirable a traumatic tip. The laser welding process depicted in FIG. 12B forms a proximal hub.

At FIG. 12C, a distal end of the filar structure is exposed to laser or other welding energy to form a distal hub. The laser energy is sufficient to melt the filars and fuse them to each other. The outer diameter of the molten material is maintained by the sleeve.

Figure 12D:
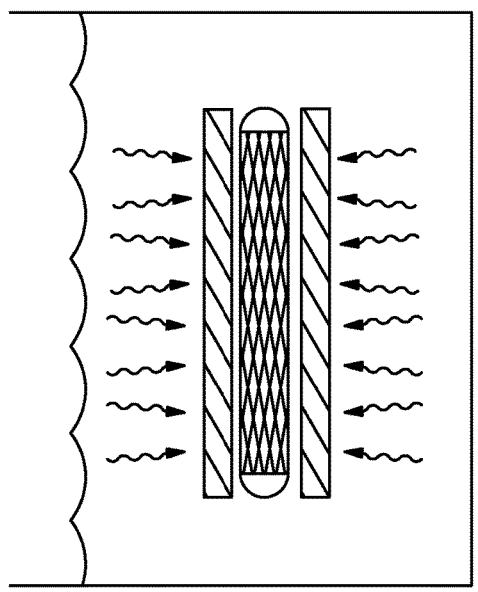
Figure 12E:
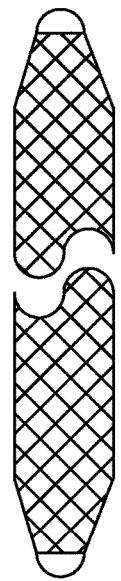

At FIG. 12D, the filar structure is freed from the sleeve. The sleeve and the welded filar structures can be placed in a high frequency bath (e.g., a sonicator). The relatively brittle material of the sleeve is shattered when exposed to the high frequency energy. The filar structure is freed from the sleeve when the sleeve shatters. In this way, the filar structure is separated from the sleeve without manipulating and causing damage to the delicate filar structure. The resulting ocular implant is shown in FIG. 12E. With reference to FIG. 12E, it will be appreciated that the middle section of the filar structure is free to expand when the sleeve is removed from around the filar structure.

FIG. 13A-FIG. 13C are a sequence of stylized plan views illustrating a method in accordance with the present detailed description. FIG. 13A-FIG. 13C may be collectively referred to as FIG. 13. The method illustrated in FIG. 13 may be used, for example, to alter the cross-sectional shape of the ocular implant formed using the methods described above.

At FIG. 13A, an ocular implant is provided. In FIG. 13A, the ocular implant is shown assuming a relaxed shape in which no external forces are acting on the ocular implant. With reference to FIG. 13A, it will be appreciate that the ocular implant has a circular cross-sectional shape when it is free to assume the relaxed shape.

At FIG. 13B, external forces are used to flatten the filar structure of the ocular implant or alternatively the implant held in flattened state and exposed to an appropriate heat profile to heat set the device to a desirable cross sectional profile. The flattening of the ocular implant results in plastic deformation of the filar structure. At FIG. 13C, the external forces are removed, allowing the ocular implant to assume a relaxed state. In the embodiment of FIG. 13C, the relaxed shape has a generally elliptical or ovoid shape. By comparing FIG. 13C with FIG. 13A, it will be appreciated that the relaxed shape of the ocular implant has changed due to plastic deformation of the filar structure.

FIG. 14A-FIG. 14E are a sequence of plan views illustrating a method in accordance with the present detailed description. FIG. 14A-FIG. 14E may be collectively referred to as FIG. 14. The method illustrated in FIG. 14 may be used, for example, to place an ocular implant into Schlemm's canal SC of an eye 20 shown in FIG. 14A. The methods illustrated in FIGS. 14A-14E may be generally referred to as ab interno methods. In some embodiments of an ab interno method, the ocular implant can be sized and configured to occupy approximately 3-6 clock hours of length within Schlemm's canal. Ocular implants in accordance with this detailed description may also be delivered using ab externo methods. In some embodiments of an ab externo method, the ocular implant can be sized and configured to occupy approximately 6-12 clock hours of length within Schlemm's canal.

Figure 14A:
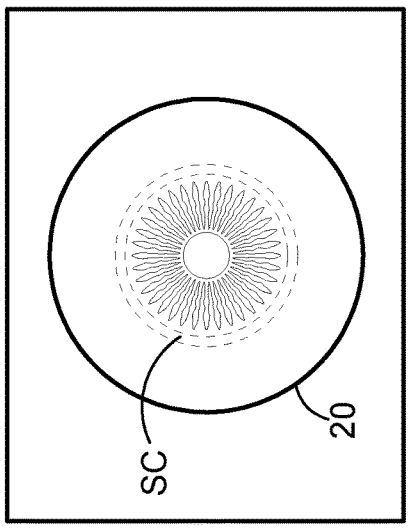
FIGS. 14A-14E are a sequence of plan views illustrating a method in accordance with the present detailed description.
Figure 14B:
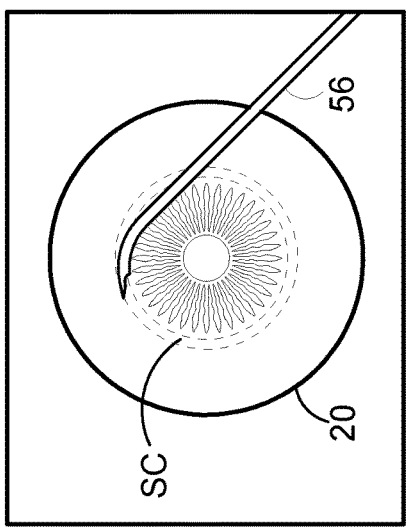

In FIG. 14B, a cannula 56 is shown extending through a cornea of eye 20 so that the distal end of cannula 56 is disposed in the anterior chamber of eye 20. In FIG. 14B, a distal portion of cannula 56 has passed through the cornea of eye 20 and has pierced the trabecular meshwork to enable a distal opening of the cannula to communicate with Schlemm's canal SC.

In the embodiment of FIG. 14B, the distal tip of cannula 56 has pierced through the trabecular meshwork of eye 20 so that a distal opening of cannula 56 is disposed in fluid communication with Schlemm's canal SC. In this embodiment, cannula 56 is a rigid curved tube that has a sharp portion at its distal end near the distal opening 58. In some embodiments, cannula 56 is curved to achieve substantially tangential entry into Schlemm's canal SC.

Figure 14C:
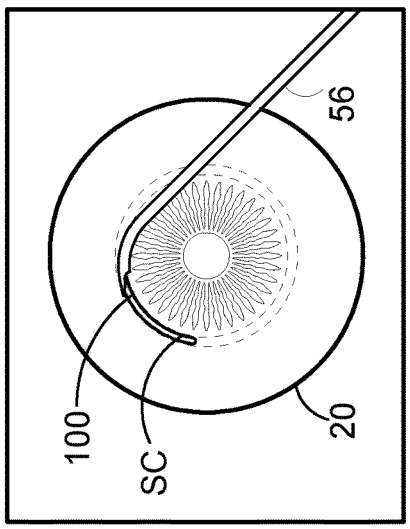

FIG. 14C is an additional plan view of eye 20 shown in the previous figure. In the embodiment of FIG. 14C, an ocular implant 100 has been advanced through the distal opening of cannula 56 and into Schlemm's canal SC of eye 20. Cannula 56 is part of a delivery system that may be used to deliver ocular implant 100 into Schlemm's canal of eye 20. The delivery system also includes an advancement mechanism for selectively applying distally directed forces to the proximal end of ocular implant 100. Further details of aspects of ocular implant delivery systems suitable for use with implants and cannulas of this invention may be found in U.S. application Ser. No. 11/943,289, filed Nov. 20, 2007; U.S. application Ser. No. 12/398,847, filed Mar. 5, 2009; U.S. Provisional Application No. 61/224,156, filed Jul. 9, 2009; and U.S. Provisional Application No. 61/224,158, filed Jul. 9, 2009; the disclosures of which are incorporated herein by reference.

Figure 14D:
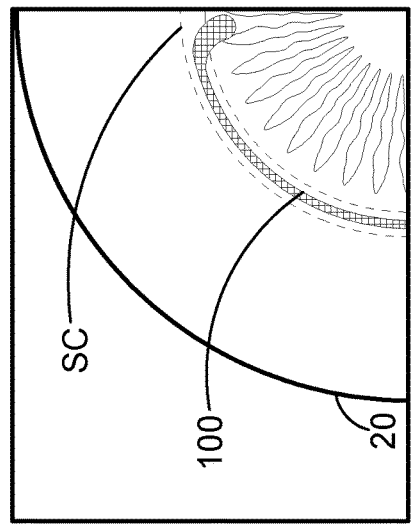
Figure 14E:
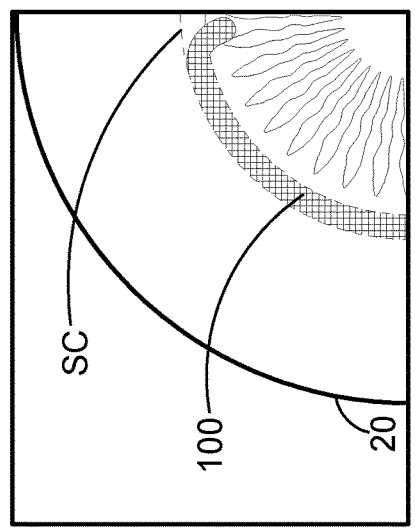

FIG. 14D is an enlarged plan view of eye 20 shown in the previous figure. In the embodiment of FIG. 14D, ocular implant 100 has been ejected from cannula 56 while assuming a collapsed state. The ocular implant 100 may include, for example, a sacrificial material disposed on the implant to constrain the implant in the collapsed state. Cannula 56 (shown in FIG. 14C) has been withdrawn from eye 20 leaving a proximal portion of ocular implant 100 extending into the anterior chamber and the remainder of ocular implant 100 residing in Schlemm's canal. With reference to FIG. 14E, it will be appreciated that the proximal portion of ocular implant 100 expands to hold the ocular implant in position.

In FIG. 14E, ocular implant 100 is shown assuming an expanded state. By comparing FIG. 14E with FIG. 14D, it will be appreciated that ocular implant 100 was advanced into Schlemm's canal SC while ocular implant 100 was fixed in a collapsed state (at FIG. 14D). At FIG. 14E, ocular implant 100 has been allowed to assume an expanded state while a distal portion of ocular implant 100 is disposed inside Schlemm's canal. In the embodiment where the implant is inserted into Schlemm's canal with a sacrificial material confining the implant into a collapsed state, the ocular implant can be pre-biased to automatically assume the expanded state when the sacrificial material dissolves from the implant. In other embodiments, tension may be applied to the distal and proximal ends of the ocular implant to stretch the implant and cause it to be fixed in the collapsed state. The presence of ocular implant 100 in Schlemm's canal may facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 100 will support trabecular mesh tissue and Schlemm's canal tissue and will provide for improved communication between the anterior chamber and Schlemm's canal (via the trabecular meshwork) and between pockets or compartments along Schlemm's canal.

FIGS. 15A-15M are a sequence of stylized plan views illustrating a method in accordance with the present detailed description. FIGS. 15A-15M may be collectively referred to as FIG. 15. The method illustrated in FIG. 15 may be used, for example, for assembling a catheter and for placing an ocular implant into Schlemm's canal of an eye using a catheter. The delivery methods illustrated in FIGS. 15A-15M may be generally referred to as ab externo methods. Ocular implants in accordance with this detailed description may also be delivered using ab interno methods (e.g., the method illustrated in FIG. 14).

FIG. 15A is a stylized plan view showing an ocular implant 100 and a delivery catheter 143. Delivery catheter 143 includes a first portion 150 and a second portion 152. A first stabilizing suture 154 is threaded through ocular implant 100 near a first end thereof. A second stabilizing suture 156 is threaded through ocular implant 100 near a second end thereof. In the embodiment of FIG. 15A, ocular implant 100 is in an expanded state. Ocular implant 100 may be urged to assume a collapsed state by applying tension to first stabilizing suture 154 and second stabilizing suture 156.

Tension applied to ocular implant 100 by first stabilizing suture 154 and second stabilizing suture 156 will stretch ocular implant 100 and reduce its diameter. Ocular implant 100 may be stretched until its outer diameter becomes smaller that the inner diameter of catheter portions 150 and 152. First portion 150 and second portion 152 of delivery catheter 143 may then be brought together so that ocular implant 100 is enclosed inside delivery catheter 143.

In the embodiment of FIG. 15B, ocular implant 100, first catheter portion 150 and second catheter portion 152 have been assembled into a single entity. This single entity may be produced, for example, by urging the two portions of delivery catheter 143 over ocular implant 100 while tension is applied to ocular implant 100 using first stabilizing suture 154 and second stabilizing suture 156. In FIG. 15B, ocular implant 100 is shown disposed in lumens defined by first portion 150 and second portion 152 of delivery catheter 143. When ocular implant is enclosed in the lumens of first portion 150 and second portion 152, the tension on first stabilizing suture 154 and second stabilizing suture 156 may be released. When the tension on the sutures is release, ocular implant 100 will be free to expand. As ocular implant 100 expands, it may grip the inner diameter of first catheter portion 150 and second catheter portion 152. The ends of first portion 150 and second portion 152 meet to form a split portion 146 of delivery catheter 143. Ocular implant 100, first catheter portion 150 and second catheter portion 152 can all be advanced and retracted through Schlemm's canal as a single entity.

FIG. 15C is a stylized plan view showing a delivery catheter 143 for delivering an ocular implant 100 in the eye. FIG. 15D is an enlarged plan view further illustrating a portion D of delivery catheter 143 shown in FIG. 15C. In the embodiment of FIG. 15, delivery catheter 143 is constructed from three portions that can be separated during the delivery procedure. The three portions include a first portion 150, a second portion 152 and a third portion 153. First portion 150 and third portion 153 are coupled together at a coupling sleeve 190.

Coupling sleeve 190 of delivery catheter 143 includes a side access window 186. A fiber optic 192 is provided that can be introduced and subsequently removed via the side access window 186 in coupling sleeve 190. In some useful embodiments, the distance from the distal tip 188 of third portion 153 to the side access window 186 in coupling sleeve 190 is established such that the entire length of Schlemm's canal can be traversed while the side access window 186 remains outside of Schlemm's canal. In use, fiber optic 192 produces a spot of light that is visible through the scleral tissue of the eye as the distal tip 188 of third portion 153 is advanced into Schlemm's canal. This spot of light provides visual feedback regarding the current location of the catheter distal end to facilitate navigation of Schlemm's canal. When the distal end of third portion 153 has exited Schlemm's canal, fiber optic 192 no longer serves this purpose so it may be withdrawn via the side access window 186 in coupling sleeve 190. With the fiber optic 192 removed the coupling sleeve and the entire delivery catheter can be advanced through Schlemm's canal.

Figure 15E:
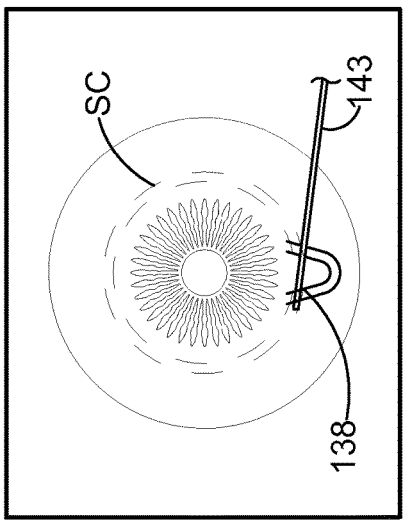

At FIG. 15E, a first cavity 126 is formed in the sclera 22 of eye 20. First cavity 126 can be formed, for example, by cutting a flap in sclera 22 of eye 20. In the embodiment of FIG. 15E, first cavity 126 has been formed by making a first incision 130 and a second incision 132 that define a generally V-shaped scleral flap. The scleral flap may be folded upward leaving an open cavity in the sclera. The scleral flap may be temporarily held in the folded position using a suture. When the procedure is complete, the cavity may be closed by folding the flap down and suturing the flap in place. For purposes of illustration, the scleral flap is not shown in FIG. 15.

Figure 15F:
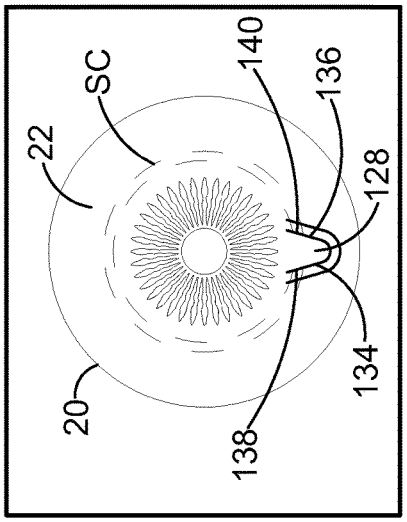
Figure 15G:
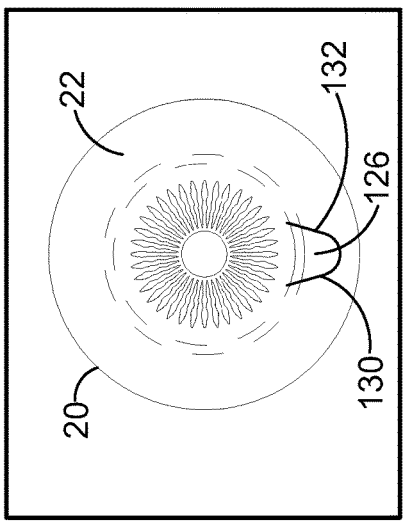

At FIG. 15F, a second cavity 128 is formed in sclera 22 of eye 20. In the embodiment of FIG. 15F, second cavity 128 has been formed by making a third incision 134 and a fourth incision 136 that define a second scleral flap. The second scleral flap may be removed leaving second cavity 128. In the method of FIG. 15, the incisions forming second cavity 128 extend deeply enough to form a first ostium 138 and a second ostium 140 in Schlemm's canal SC. A catheter or other device may be inserted through first ostium 138 and/or second ostium 140 to enter Schlemm's canal. At FIG. 15G a delivery catheter 143 is inserted into Schlemm's canal SC through first ostium 138.

Figure 15H:
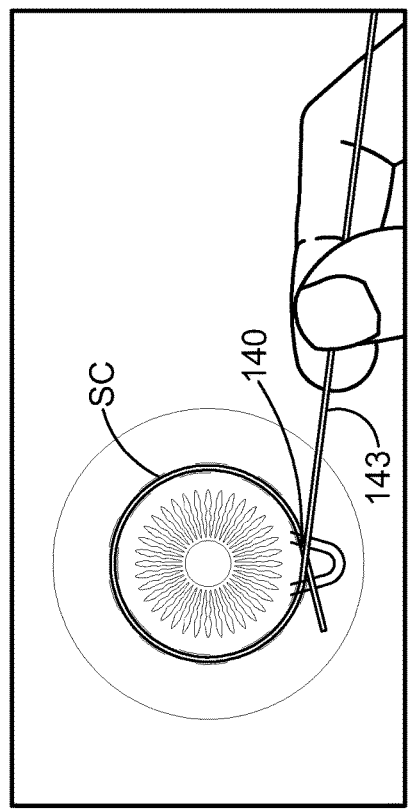

At FIG. 15H, delivery catheter 143 is advanced through Schlemm's canal SC. With reference to FIG. 15H, it will be appreciated that delivery catheter 143 has been advanced so that the distal end of the delivery catheter 143 has exited second ostium 140. A portion of delivery catheter 143 extending beyond second ostium 140 is visible in FIG. 15H.

Figure 15I:
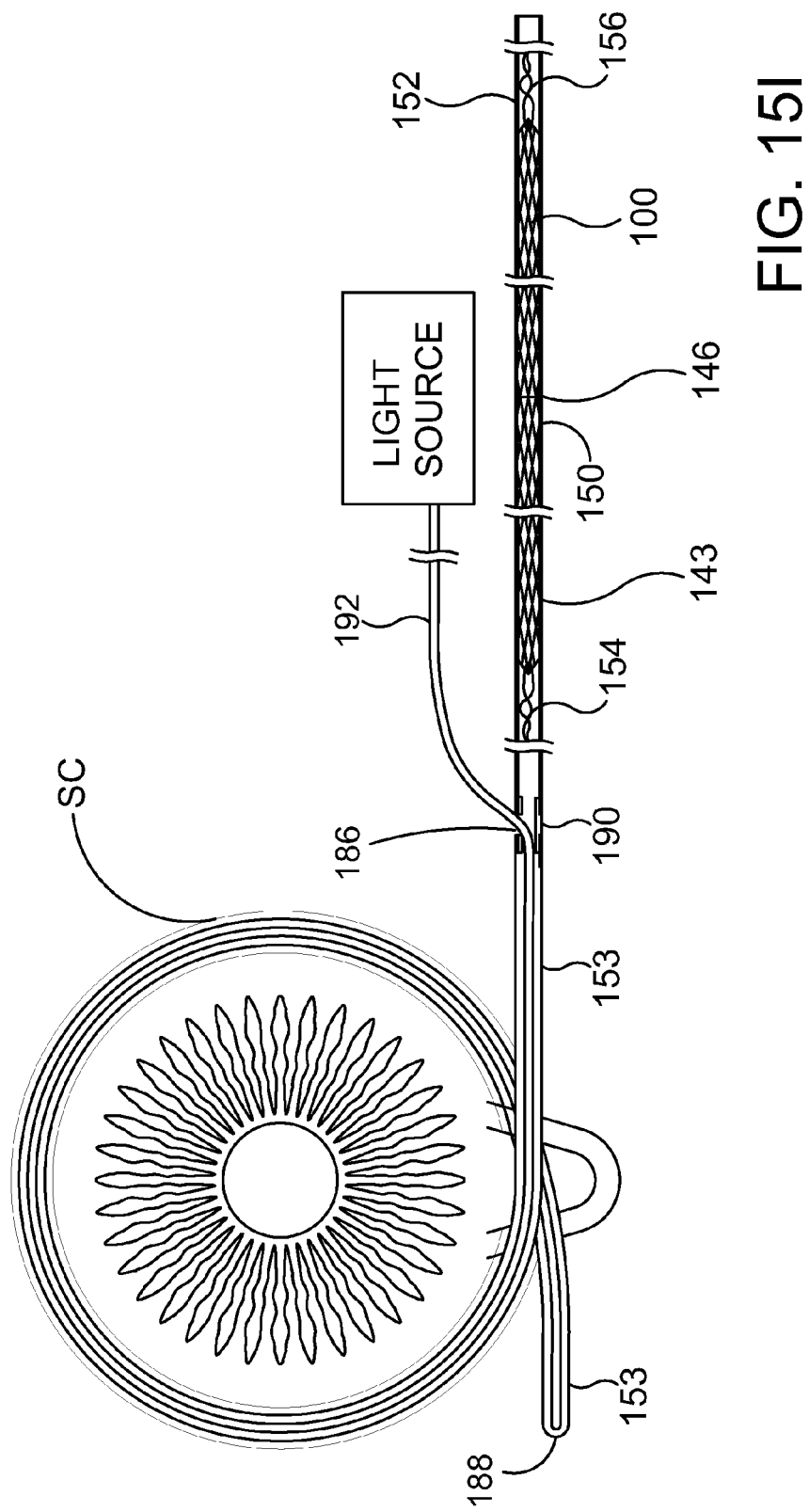
Figure 15J:
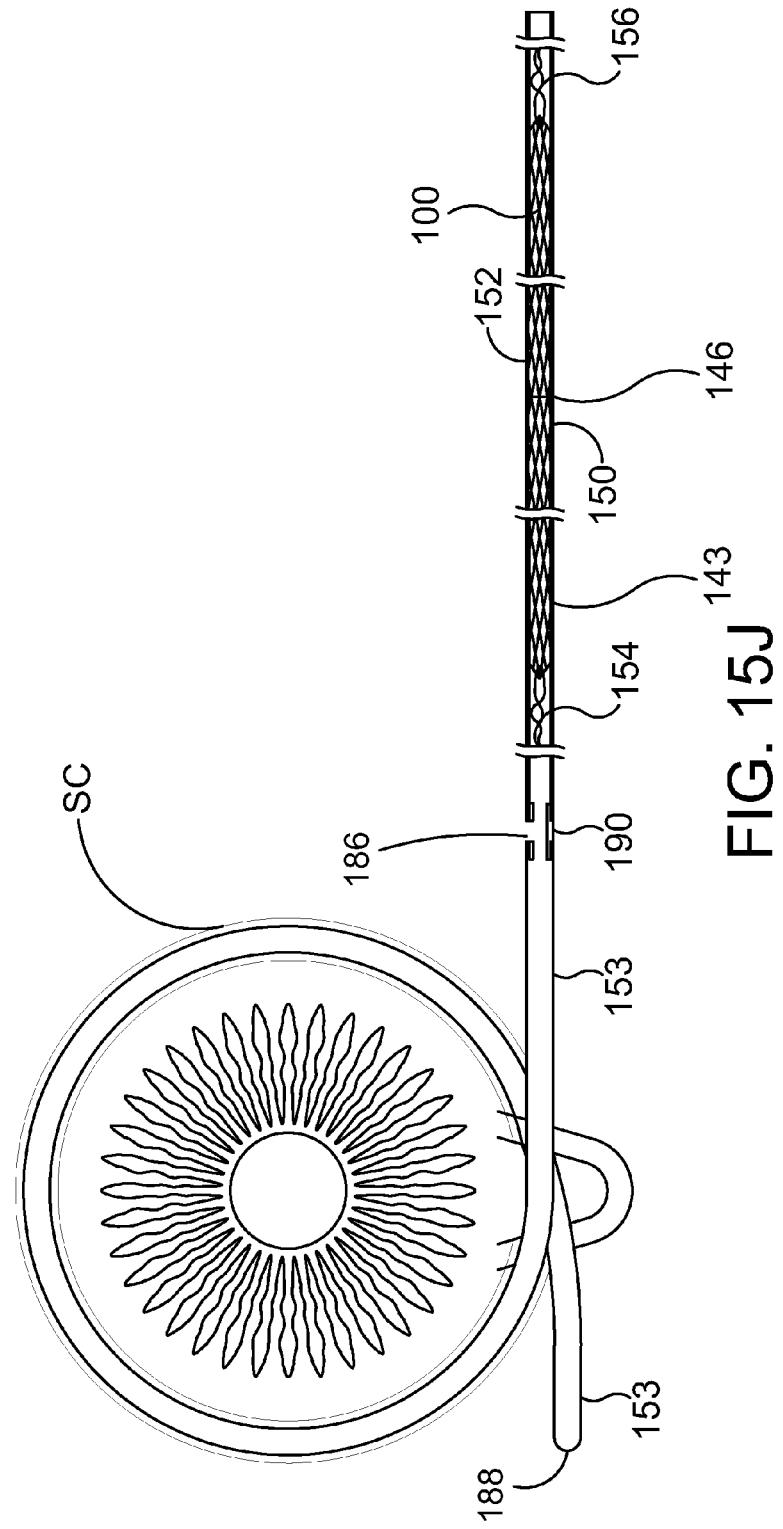

FIG. 15I is a stylized plan view of Schlemm's canal SC and delivery catheter 143 shown in the previous figure. Delivery catheter 143 is enlarged and made transparent in FIG. 15I in order to illustrate additional details of the delivery catheter. Delivery catheter 143 includes a first portion 150 and a second portion 152. In FIG. 15I, ocular implant 100 is shown disposed in lumens defined by first portion 150 and second portion 152 of delivery catheter 143. A first stabilizing suture 154 is threaded through ocular implant 100 near a first end thereof. A second stabilizing suture 156 is threaded through ocular implant 100 near a second end thereof. The ends of first portion 150 and second portion 152 meet to form a split portion 146 of delivery catheter 143.

In the embodiment of FIG. 15, delivery catheter 143 is constructed from three portions that can be separated during the delivery procedure. The three portions include a first portion 150, a second portion 152 and a third portion 153. First portion 150 and third portion 153 are coupled together at a coupling sleeve 190. Coupling sleeve 190 of delivery catheter 143 includes an access window 186. In FIG. 15I, a fiber optic 192 is shown extending through a side access window 186 in coupling sleeve 190. In some useful embodiments, the distance from the distal tip 188 of third portion 153 to the side access window in coupling sleeve 190 is established such that the entire length of Schlemm's canal can be traversed while the side access window remains outside of Schlemm's canal. In use, fiber optic 192 produces a spot of light that is visible through the scleral tissue of the eye as the distal tip 188 of third portion 153 is advanced into Schlemm's canal. This spot of light provides visual feedback regarding the current location of the catheter distal end to facilitate navigation of Schlemm's canal. When the distal end of third portion 153 has exited Schlemm's canal, fiber optic 192 no longer performs this function so it may be withdrawn via the side access window in coupling sleeve 190. With the fiber optic 192 removed the coupling sleeve and the entire delivery catheter can be advanced through Schlemm's canal. FIG. 15J shows delivery catheter 143 after fiber optic 192 has been removed.

Figure 15K:
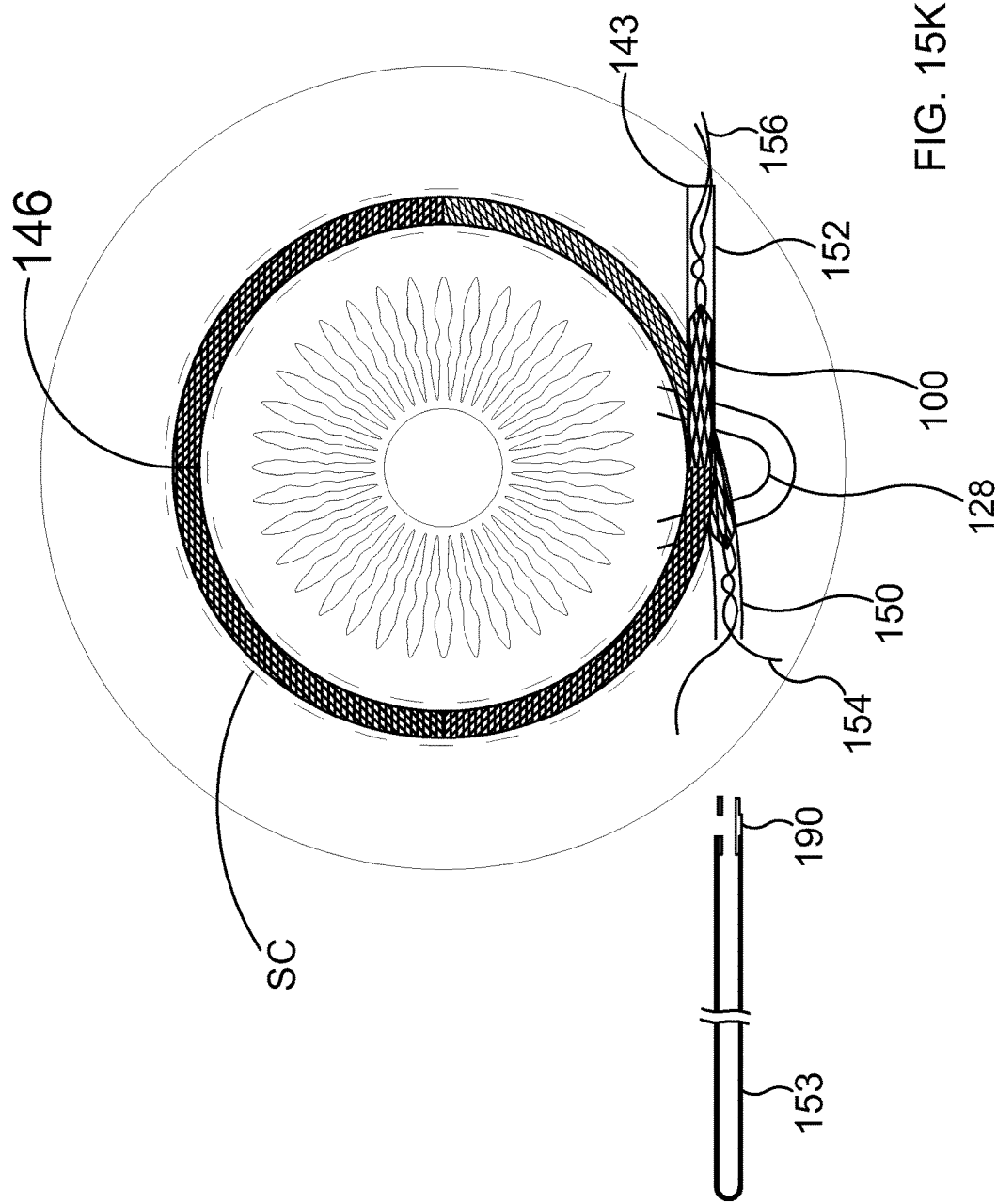

At FIG. 15K, delivery catheter 143 has been advanced into Schlemm's canal until split portion 146 of delivery catheter 143 is opposite second cavity 128. In the embodiment of FIG. 15K, coupling 190 and third portion 153 of delivery catheter 143 have been separated from first portion 150 of delivery catheter 143. With reference to FIG. 15K, it will be appreciated that first stabilizing suture 154 is now exposed. Second stabilizing suture 156 is shown extending out of second portion 152 in the embodiment of FIG. 15K. Each stabilizing suture extends into the lumen defined by delivery catheter 143. In the embodiment of FIG. 15K, first stabilizing suture 154 is threaded through ocular implant 100 near a first end thereof. Second stabilizing suture 156 is threaded through the ocular implant near a second end thereof.

Figure 15L:
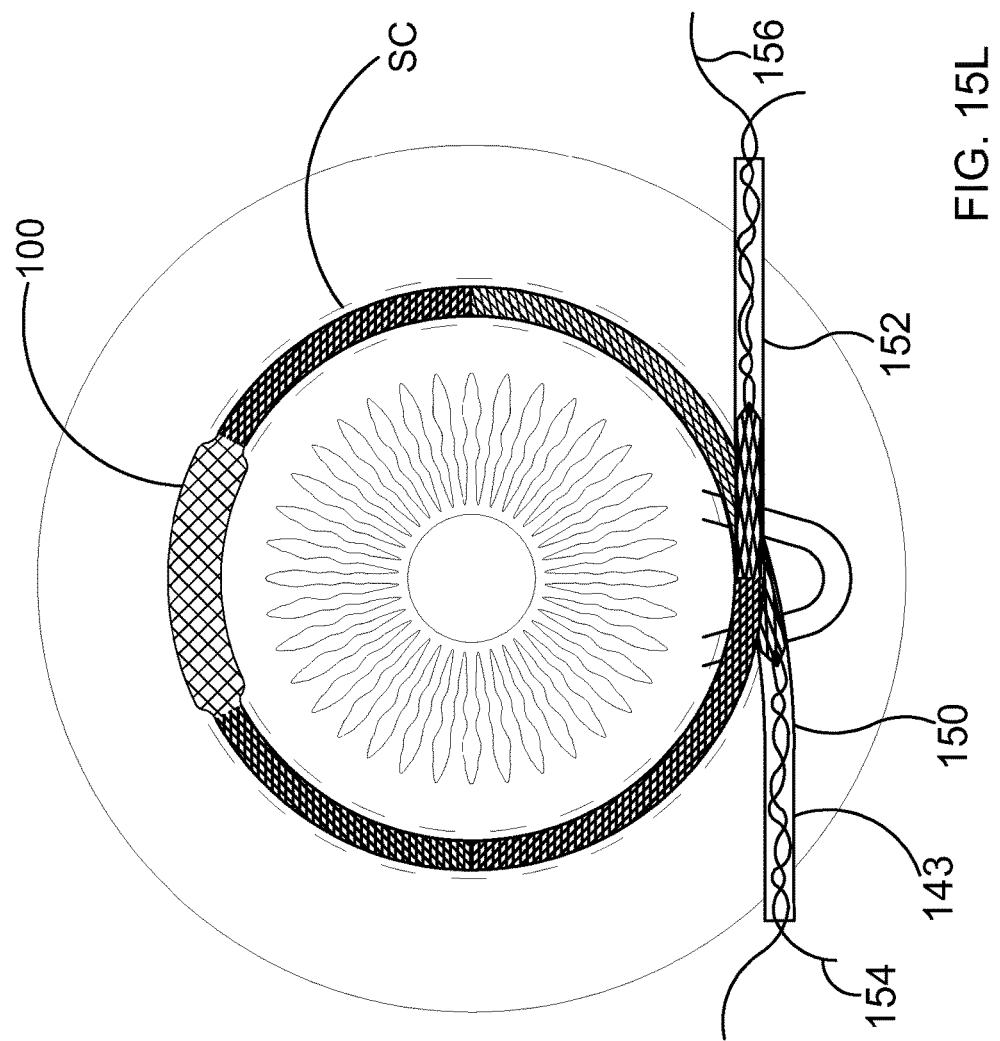

In the embodiment of FIG. 15K, delivery catheter 143 can be advanced and retracted as necessary to appropriately position ocular implant 100. Referring now to FIG. 15L, it will be appreciated that when the correct positioning of ocular implant 100 has been achieved both first portion 150 and second potion 152 of delivery catheter 143 can be retracted from Schlemm's canal by simultaneously keeping traction on first stabilizing suture 154 and second stabilizing suture 156 to maintain correct positioning of ocular implant 100. When successful retraction of the first and second catheter portions is complete the exposed sutures may be withdrawn by pulling on one end until the other end is pulled through ocular implant 100 and out of the eye. Alternatively, if biodegradable sutures are used, exposed portions of the sutures may be cut off and the encased portions of the sutures may be left to degrade.

At FIG. 15L, first portion 150 and second portion 152 of delivery catheter 143 are being withdrawn from Schlemm's canal SC. First portion 150 and second portion 152 of delivery catheter 143 may be withdrawn from Schlemm's canal simultaneously, releasing ocular implant 100 within Schlemm's canal. If adjustments need to be made, pulling forces can be selectively applied to the ocular implant by first stabilizing suture 154 and second stabilizing suture 156. With reference to FIG. 15L, it will be appreciated that a portion of ocular implant 100 is free to assume a radially expanded shape as first portion 150 and second portion 152 are withdrawn.

Figure 15M:
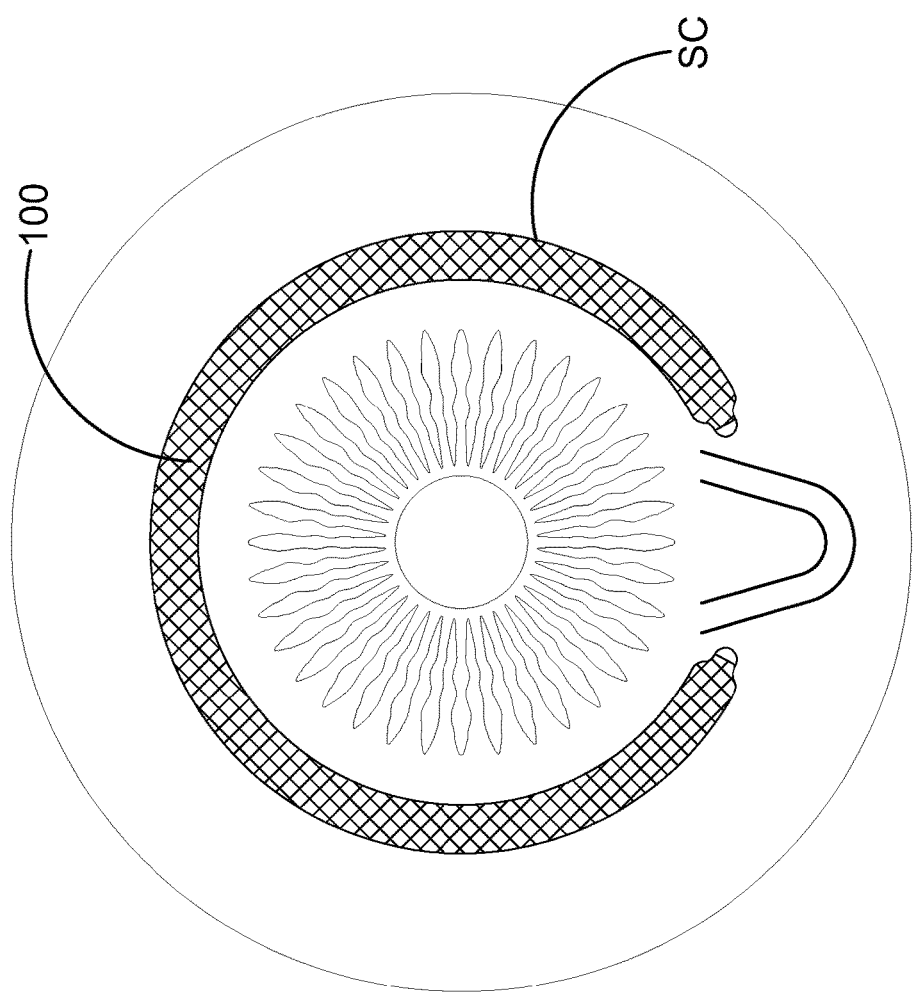

In FIG. 15M, ocular implant 100 is shown residing in Schlemm's canal SC. With reference to FIG. 15M, it will be appreciated that the first and second portions of the delivery catheter have been completely removed from Schlemm's canal. After ocular implant 100 has been placed in the desired location, the stabilizing sutures may be removed. Each suture may be removed by pulling on one end of the suture until the other end of the suture is pulled through the ocular implant and out of Schlemm's canal. Alternatively the sutures could be biodegradable and only the visibly exposed suture would be cut and removed.

As for additional details pertinent to the present disclosure, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An ocular implant, comprising:
   an implant body sized and configured to be inserted into Schlemm's canal of an eye, the implant body comprising a plurality of filars, each filar having a proximal end, a distal end and an intermediate portion extending between the proximal end and the distal end, the distal ends of the filars being fixed to each other and the proximal ends of the filars being fixed to each other; and
   sacrificial material constraining at least a portion of the implant body in a radially collapsed state;
   the ocular implant being configured to move between the radially collapsed state and a radially expanded state, wherein the ocular implant is configured to assume the radially expanded state when the sacrificial material erodes or dissolves.

2. The ocular implant of claim 1, wherein constraining forces are applied to the intermediate portions of the filars by the sacrificial material that adheres the individual filars together in a matrix which restricts motion between the individual filars so that expansion of the ocular implant is prohibited.

3. The ocular implant of claim 1, wherein:
   the ocular implant has a first pushability when the ocular implant is in the radially expanded state;
   the ocular implant has a second pushability when the ocular implant is in the radially collapsed state; and
   the second pushability is greater than the first pushability so as to facilitate advancement of the ocular implant into Schlemm's canal.

4. The ocular implant of claim 1, wherein:
   the ocular implant has a first lateral dimension when the ocular implant is in the radially expanded state;
   the ocular implant has a second lateral dimension when the ocular implant is in the radially collapsed state; and
   the second lateral dimension is smaller than the first lateral dimension so as to facilitate advancement of the ocular implant into Schlemm's canal.

5. The ocular implant of claim 1, wherein a volume defined by the ocular implant has a circular cross-section.

6. The ocular implant of claim 1, a volume defined by the ocular implant has a non-circular cross-section.

7. The ocular implant of claim 1, a volume defined by the ocular implant has a generally ovoid or elliptical cross-section.

8. The ocular implant of claim 1, wherein the proximal ends of the filars are fixed to a proximal hub and the distal ends of the filars are fixed to a distal hub.

9. The ocular implant of claim 8, wherein each hub comprises a weld bead formed of material from the filars.

10. The ocular implant of claim 8, wherein each filar follows a path that curves through three dimensional space as the filar extends distally between the proximal hub and the distal hub.

11. The ocular implant of claim 10, wherein the path followed by each filar substantially conforms to the shape of a helix.

12. The ocular implant of claim 1, wherein a proximal portion of the ocular implant is not fixed in the radially collapsed state so as to be free to expand into contact with Schlemm's canal to prevent migration of the ocular implant while the sacrificial material is dissolving.

* * * * *